United States Patent
Wang et al.

(10) Patent No.: US 11,969,236 B2
(45) Date of Patent: Apr. 30, 2024

(54) DEVICE FOR MEASURING BLOOD PRESSURE

(71) Applicant: Accurate Meditech Inc, New Taipei (TW)

(72) Inventors: Kuan Jen Wang, New Taipei (TW); Cheng Yan Guo, New Taipei (TW); Ching-Hung Huang, New Taipei (TW)

(73) Assignee: Accurate Meditech Inc, New Taipei (TW)

( * ) Notice: Subject to any disclaimer, the term of this patent is extended or adjusted under 35 U.S.C. 154(b) by 824 days.

(21) Appl. No.: 17/058,638

(22) PCT Filed: May 24, 2019

(86) PCT No.: PCT/CN2019/088399
§ 371 (c)(1),
(2) Date: Nov. 24, 2020

(87) PCT Pub. No.: WO2019/223796
PCT Pub. Date: Nov. 28, 2019

(65) Prior Publication Data
US 2021/0204824 A1    Jul. 8, 2021

(51) Int. Cl.
*A61B 5/022*    (2006.01)
*A61B 5/00*    (2006.01)
(Continued)

(52) U.S. Cl.
CPC ........ *A61B 5/02233* (2013.01); *A61B 5/0022* (2013.01); *A61B 5/0082* (2013.01);
(Continued)

(58) Field of Classification Search
CPC . A61B 5/02233; A61B 5/0022; A61B 5/0082; A61B 5/02007; A61B 5/02125;
(Continued)

(56) References Cited

U.S. PATENT DOCUMENTS 10,555,676 B2 *   2/2020   McCombie .......... A61B 5/1123
10,786,161 B1 *   9/2020   Archdeacon ......... A61B 5/0205
(Continued)

FOREIGN PATENT DOCUMENTS

CN        104138253 A    11/2014
EP          3288447 A1     3/2018
(Continued)

OTHER PUBLICATIONS

Papaioannou Theodore G et al: "Mean arterial pressure values calculated using seven different methods and their associations with target organ deterioration in a single-center study of 1878 individuals", Hypertension Research., vol. 39, No. 9, May 19, 2016 (May 19, 2016), pp. 640-647, XP037325815, ISSN: 0916-9636, DOI: 10.1038/HR.2016.41; abstract, section "Introduction", p. 640-p. 641.

(Continued)

*Primary Examiner* — Yi-Shan Yang
*Assistant Examiner* — Joseph A Tombers
(74) *Attorney, Agent, or Firm* — ScienBiziP, P.C.

(57) ABSTRACT

A wearable device for measuring blood pressure comprises a housing with through-holes formed thereon, a processing unit disposed in the housing, a display connected to the processing unit, a plurality of sensors connected to the processing unit, the sensors being configured to transmit at least one physiological signal to the processing unit via the through-holes, and a time delay structure connected between one of the through-holes and one of the sensors and configured to lengthen a path distance between the skin surface and the sensor, wherein the processing unit is configured to determine a systolic arterial pressure and a diastolic arterial pressure by the at least one physiological signal and a Moens-Korteweg (MK) function, and to control the display (Continued)

to display the systolic arterial pressure and the diastolic arterial pressure to be read by the user.

18 Claims, 32 Drawing Sheets

(51) Int. Cl.
*A61B 5/02* (2006.01)
*A61B 5/021* (2006.01)

(52) U.S. Cl.
CPC ...... *A61B 5/02007* (2013.01); *A61B 5/02125* (2013.01); *A61B 5/742* (2013.01); *A61B 2562/0219* (2013.01); *A61B 2562/06* (2013.01)

(58) Field of Classification Search
CPC ............ A61B 5/742; A61B 2562/0219; A61B 2562/06; G16H 50/30; G16H 40/67; G16H 40/63
See application file for complete search history.

(56) References Cited

U.S. PATENT DOCUMENTS

| | | | |
|---|---|---|---|
| 2006/0106361 A1* | 5/2006 | Muni | A61B 5/416 623/1.11 |
| 2008/0039731 A1 | 2/2008 | McCombie et al. | |
| 2017/0095168 A1 | 4/2017 | Kwon et al. | |
| 2017/0095171 A1* | 4/2017 | Park | A61B 5/02007 |
| 2017/0172431 A1 | 6/2017 | Kim et al. | |
| 2017/0205767 A1 | 7/2017 | Rosen | |
| 2017/0340219 A1 | 11/2017 | Sullivan et al. | |
| 2018/0078155 A1 | 3/2018 | Baek et al. | |
| 2018/0184921 A1* | 7/2018 | Baxi | A61B 5/316 |
| 2018/0206734 A1* | 7/2018 | Lin | A61B 5/02007 |
| 2019/0117092 A1* | 4/2019 | Yamashita | A61B 5/02 |
| 2021/0378534 A1* | 12/2021 | Moreland | A61B 5/02427 |

FOREIGN PATENT DOCUMENTS

| | | |
|---|---|---|
| JP | 2011206383 A | 10/2011 |
| JP | 2015054223 A | 3/2015 |
| JP | 2016-174798 A | 10/2016 |
| JP | 2018-508273 A | 3/2018 |
| WO | 2017086071 A1 | 5/2017 |

OTHER PUBLICATIONS

Meanet E. et al: "Formula and nomogram for the sphygmomanometric calculation of the mean arterial pressure", British Heart Journal., vol. 84, No. 1, Jul. 1, 2020 (Jul. 1, 2020), pp. 64-64, XP055808748, GB, ISSN: 1355-6037, DOI: 10.1136/heart.84.1.64; the whole document.
Anonymous: "Electronic visual display—Wikipedia", Mar. 26, 2018 (Mar. 26, 2018), XP055808983, the whole document.
Ron Dueck et al: "Noninvasive continuous beat-to-beat radial artery pressure via TL-200 applanation tonometry", Journal of Clinical Monitoring and Computing, Kluwer Academic Publishers, DO, vol. 26, No. 2, Jan. 18, 2012 (Jan. 18, 2012), pp. 75-83, XP035029412, ISSN: 1573-2614, DOI: 10.1007/S10877-012-9336-2; the whole document.
Bartels Karsten et al: "Advances in photoplethysmography: beyond arterial oxygen saturation", Canadian Journal of Anaesthesia / Journal Canadien D'Anesthesie, Canadian Anaesthetists Society, Toronto, CA, vol. 62, No. 12, Aug. 19, 2015 (Aug. 19, 2015), pp. 1313-1328, XP035787069, ISSN: 0832-610X, DOI: 10.1007/S12630-015-0458-0; the whole document.
Anonymous: "Mean Arterial Pressure Equation Page :: MediCalculator :: ScyMed :::", Jun. 13, 2017 (Jun. 13, 2017), XP055808757, the whole document.

\* cited by examiner

DEVICE FOR MEASURING BLOOD PRESSURE

CROSS-REFERENCE TO RELATED APPLICATION

The present application claims priority to U.S. Provisional Application No. 62/676,909, filed on May 25, 2018, the entirety of which is incorporated herein by reference.

FIELD OF THE INVENTION

The present disclosure relates to a physiological signal monitoring system, and more particularly, to a device that is capable of sensing various types of physiological signals of the user and transmitting the signals to mobile devices and cloud servers for healthcare or diagnostic use by medical professionals.

BACKGROUND

Monitoring chronic conditions has been a primary focus in the field of healthcare, not only for the persistency or otherwise long-lasting of the chronic conditions, but also for their potential fatality. One of the common examples of chronic condition is hypertension, which requires accurate and regular monitoring. If untreated or poorly treated, hypertension may lead to heart disease, poor blood flow, or even stroke.

Traditionally, measurement of blood pressure is performed by manual blood pressure gauge, stethoscope, and a trained practitioner. Modern electronics realize digitalized blood pressure monitoring by adopting oscillometric measurements and electronic calculations, to eliminate the needs for stethoscopes and trained practitioners. However, strapping and pumping are required in oscillometric measurements, therefore causing discomfort to the person being measured.

Furthermore, although cuff-less blood pressure measurement may ease discomfort, accuracy of the measurement remains questionable, at least for that several hemodynamic parameters are not taken into consideration in the linear or non-linear regression calculation used in the measurement.

SUMMARY OF THE INVENTION

An objective of the present disclosure is to provide a method and a wearable device for blood pressure monitoring with high measurement accuracy.

Another objective of the present disclosure is to provide an ergonomic miniature cuff-less wearable device for blood pressure monitoring.

Yet another objective of the present disclosure is to provide a wearable device for blood pressure monitoring under any posture of a user.

An embodiments of the present disclosure provides a device for measuring blood pressure. The device comprises a housing, a processing unit disposed in the housing, a display disposed on the housing and in communication with the processing unit, and a plurality of sensors in communication with the processing unit and configured to sense an artery of a user and transmit at least one physiological signal corresponding to the artery to the processing unit. The processing unit is configured to process the at least one physiological signal to obtain a plurality of hemodynamic parameters and a pulse transit time, determine a mean arterial pressure from the plurality of hemodynamic parameters and the pulse transit time via a Moens-Korteweg (MK) function, determine a systolic arterial pressure and a diastolic arterial pressure from the mean arterial pressure, and control the display to display the systolic arterial pressure and the diastolic arterial pressure.

In a preferred embodiment, the plurality of sensors comprise a mechanical wave sensor and an optical sensor.

In a preferred embodiment, the mechanical wave sensor is a piezoelectric sensor, a plurality of through-holes on the housing are disposed corresponding to the piezoelectric sensor and the optical sensor, and the through-holes form a straight line parallel to the artery.

In a preferred embodiment, the piezoelectric sensor and the optical sensor are configured to operate under different sampling rates.

In a preferred embodiment, the plurality of sensors comprise two mechanical wave sensors and an optical sensor, a plurality of through-holes on the housing are disposed corresponding to the two mechanical wave sensors and the optical sensor, and the through-holes form a straight line parallel to the artery.

In a preferred embodiment, a sampling rate of the two mechanical wave sensors is different from a sampling rate of the optical sensor.

In a preferred embodiment, the plurality of sensors comprise a piezoelectric sensor, the device further comprises a signal controller and a signal detector in communication with the piezoelectric sensor, wherein the signal detector is configured to detect a signal direction of the at least one physiological signal sent from the piezoelectric sensor, and the signal controller is configured to change the signal direction.

In a preferred embodiment, when the polarization direction of one of the piezoelectric sensor is opposite to an expected polarization direction, the signal controller changes the signal direction of a physiological signal subsequent to the physiological signal.

In a preferred embodiment, the device further comprises a time delay structure disposed between one of the sensors and one of a plurality of through-holes formed on the housing, wherein the time delay structure is configured to lengthen a path distance between a pulse of the user and the sensor, and the pulse transit time obtained by the processing unit is associated with the path distance.

In a preferred embodiment, the time delay structure is spiral shaped or zig-zag shaped.

In a preferred embodiment, the time delay structure is a tube containing a medium for transmitting mechanical waves.

In a preferred embodiment, the plurality of sensors comprise an accelerometer and a gyroscope, the accelerometer and the gyroscope are configured to measure axial changes of the device, and the processing unit is further configured to adjust the pulse transit time according to the axial changes.

In a preferred embodiment, the device enters a measuring mode and displays the systolic arterial pressure and the diastolic arterial pressure when a posture of the user determined by the processing unit according to the axial changes lasts for a period of time longer than a threshold.

In a preferred embodiment, an alarm configured to generate a retest notification when variance of the physiological signal is determined to exceed a threshold.

In a preferred embodiment, the plurality of sensors comprise a mechanical wave sensors, at least one of a plurality of through-holes formed on the housing is conical shaped, and the at least one through-holes enhances reception of the mechanical wave sensor.

In a preferred embodiment, the device further comprises a contacting material fixedly attached around an opening of the plurality of through-holes to enhance seal tightness between the opening and a skin surface of the user.

In a preferred embodiment, the device further comprises a mesh material or a film covering one of the through-holes to prevent foreign objects from entering the through-hole.

In a preferred embodiment, the mesh material is made of polytetrafluoroethylene, and the film is made of silicone rubber.

In a preferred embodiment, the hemodynamic parameters comprise an arterial stiffness level and an artery expansion level, the arterial expansion level is normalized according to the arterial stiffness level by the processing unit to obtain a pulse pressure, the pulse pressure and a coefficient k are utilized for determining the systolic arterial pressure and the diastolic arterial pressure, and the coefficient k ranges from 0 to 1.

In a preferred embodiment, the plurality of sensors are disposed in the housing and do not overlap a central line of the device.

In a preferred embodiment, each of the plurality of sensors is removably attached to the user and wirely or wirelessly connected to the device.

In a preferred embodiment, the plurality of sensors comprise a first sensor and a second sensor, the first sensor is disposed outside of the housing of the device, and the second sensors is disposed in the housing.

In sum, the device and method according to the various embodiments of the present disclosure utilize pulse transit time and hemodynamic parameters to ensure high accuracy of blood pressure monitoring, improved wearing experience, and convenient monitoring.

BRIEF DESCRIPTION OF THE DRAWINGS

The accompanying drawings illustrate one or more embodiments of the present invention and, together with the written description, explain the principles of the present invention. Wherever possible, the same reference numbers are used throughout the drawings referring to the same or like elements of an embodiment.

In accordance with common practice, the various described features are not drawn to scale and are drawn to emphasize features relevant to the present disclosure. Like reference characters denote like elements throughout the figures and text.

DETAILED DESCRIPTION OF THE PREFERRED EMBODIMENTS

Figure 1:
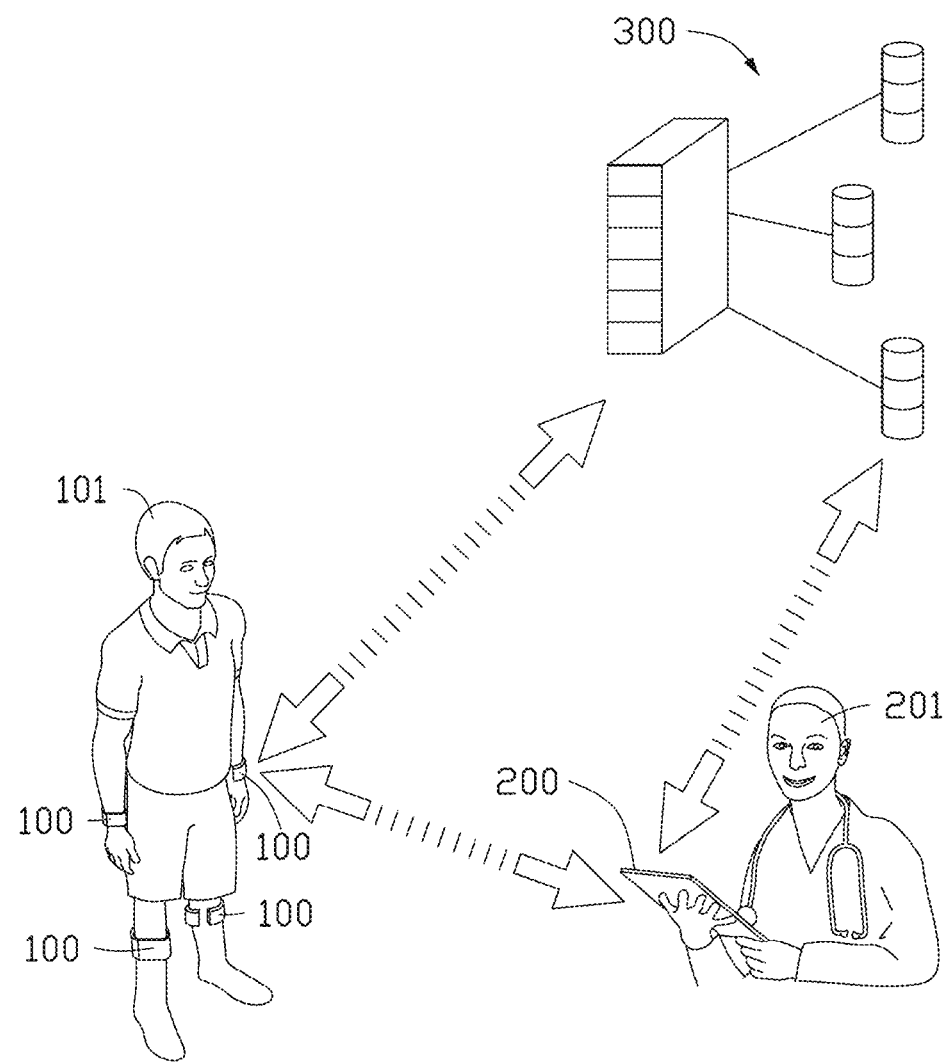
FIG. 1 is a schematic diagram of an overall configuration of the physiological signal monitoring system in accordance with an embodiment of the present disclosure.

The present invention will now be described more fully hereinafter with reference to the accompanying drawings illustrating various exemplary embodiments of the invention. The present invention may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

It will be understood that the terms "and/or" and "at least one" include any and all combinations of one or more of the associated listed items. It will also be understood that, although the terms first, second, third etc. may be used herein to describe various elements, components, regions, parts and/or sections, these elements, components, regions, parts and/or sections should not be limited by these terms. These terms are only used to distinguish one element, component, region, part or section from another element, component, region, layer or section. Thus, a first element, component, region, part or section discussed below could be termed a second element, component, region, layer or section without departing from the teachings of the present disclosure.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Referring to FIG. 1, a schematic diagram showing the overall configuration of a physiological signal monitoring system in accordance with an embodiment of the present disclosure. The physiological signal monitoring system may include a wearable device 100, a mobile device 200 and a cloud server 300. The wearable device 100 is configured to collect physiological signals of a user 101. The physiological signals collected by the wearable device 100 may be transmitted to the mobile device 200 (e.g., smart phone, smart speaker, smart robot or the like) and the cloud server 300 (e.g., Amazon Web Service (AWS), Google Cloud Platform (GCP) or the like). The cloud server 300 may be configured to store and analyze physiological information associated with the physiological signals, and to identify the user's identity based on the physiological information for further classification, diagnosis and monitoring by health care professionals 201.

In at least one embodiment of the present disclosure, the wearable device 100 may include various types of sensors including, for example, nanosecond pulse near-field sensing (NPNS) based sensor, near-infrared spectroscopy (NIRS) based sensor, piezoelectric sensor, accelerometer, gyroscope, barometer, temperature sensor, Doppler sensor, ultrasound transducer, laser diode sensor, photodiode sensor, GPS or the like. In at least one embodiment of the present disclosure, the physiological signal monitoring system may include one or more wearable devices 100. The wearable devices 100 may include, but are not limited to, watch, sleevelet, belt, bracelet, ankle bracelet, tourniquet, scarf, collar, necklace, shoe or the like. The wearable device 100 may be worn on extremities, waist and/or neck of the user's body to continuously collect the user's physiological signals for determining the user's physiological information, including heartbeat, blood oxygen, electroencephalography (EEG), electromyography (EMG), electrocardiography (ECG), photoplethysmography (PPG), skin impedance, systolic blood pressure (SBP), diastolic blood pressure (DBP), mean arterial pressure (MAP), body fat, pulse beat, pulse arrival time (PAT), pulse transit time (PTT), pulse wave velocity (PVW), breath, irregular pulse peak (IPP), irregular heart beat (IHB), atrial fibrillation (AF) and heart rate variability (HRV). The physiological information of the user is determined based on the physiological signals. The physiological signals may be transmitted to the mobile device(s) 200 or the cloud server 300 via wireless communication, such as Bluetooth Low Energy (BLE), Bluetooth (BT), Wi-Fi®, Long Range (LoRa®), 4G/LTE®, Zigbee or the like. Characteristics of the physiological signals may be retrieved through feature extraction algorithm on the mobile device 200 and the cloud server 300, and the physiological signals may be classified accordingly for the user's identification. The physiological information is interpretable by the health care professionals 201, and may be stored on the mobile device 200 and/or the cloud server 300 according to the user's identity for diagnostic or analytical use by the health care professionals 201.

In at least one embodiment of the present disclosure, the physiological signals received from the sensors 110, such as NPNS based sensor, NIRS based sensor, piezoelectric sensor, accelerometer, gyroscope, barometer, temperature sensor, Doppler sensor, ultrasound transducer, laser diode sensor, photodiode sensor and GPS, are processed by a processing unit of the wearable device 100 to obtain the physiological information including heartbeat, blood oxygen, EEG, EMG, ECG, PPG, skin impedance, systolic blood pressure (SBP), diastolic blood pressure (DBP), mean arterial pressure (MAP), body fat, pulse beat, pulse arrival time (PAT), pulse transit time (PTT), pulse wave velocity (PWV), breath, irregular pulse peak (IPP), irregular heart beat (IHB), atrial fibrillation (AF) and heart rate variability (HRV). As shown in FIG. 1, the physiological information obtained by the wearable device 100 may be transmitted to a gateway (not shown) and then to the cloud server 300 (e.g., GCP, AWS) via wireless communication such as Bluetooth Low Energy (BLE), Bluetooth (BT), Wi-Fi®, Long Range (LoRa®), 4G/LTE®, Zigbee or the like, or transmit directly to the mobile device 200, such as smart phones, smart speakers, smart robots or the like. Such physiological information may also be transmitted from the mobile device 200 to the gateway, and then to the cloud server 300.

In at least one embodiment of the present disclosure, when the wearable device 100 is connected to the cloud server 300 or the mobile device 200 for the first time, the cloud server 300 or the mobile device 200 calibrates via network time protocol (NTP), then the wearable device 100 would start collecting the physiological signals in time sequence and transmitting corresponding physiological information to the cloud server 300 or the mobile device 200 via the gateway so as to store the physiological information in the corresponding database.

In at least one embodiment of the present disclosure, the physiological signals and the physiological information may be transmitted in JavaScript Object Notation (JSON) format. The JSON format includes two packets, one of which is a RAW data packet for transmitting original physiological signals, and the other of which is an Info packet for transmitting processed signals (or the physiological information). The two packets are described as follows.

Format 1: RAW Data
   {"Sensor 1": "0~4096"
   "Sensor 2": "0~4096"
   "Sensor 3": "0~4096"
   "Sensor 4": "0~4096"
   . . .
   "Sensor N": "0~4096"
   "Type": "RAW Data"
   }

Format 2: Info
   {"Sys": "0~300"
   "Dia": "0~300"
   "Pulse": "45~150"
   "SpO$_2$": "0~100"
   . . .
   "Breath": "6~36"
   "Type": "Info"
   }

Referring to FIG. 1, in at least one embodiment of the present disclosure, various user specific data sheets may be built in the database of the cloud server 300 or the mobile device 200. When the physiological information is sent to the cloud server 300 or the mobile device 200, the cloud server 300 or the mobile device 200 finds the corresponding data sheet to save the physiological information. In addition, the cloud server 300 or the mobile device 200 may compare the parameters in the physiological information to determine if the parameters are within reasonable ranges, and to determine the user's identity by using a feature extraction algorithm. When the parameters are outside the reasonable ranges or the user's identity cannot be determined by the feature extraction algorithm, the cloud server 300 or the mobile device 200 may either send a notification or a reminder to the wearable device 100, or simply display the notification or reminder on the mobile device 200, to notify the user 101 or the health care professionals 201. When the notification or reminder is sent, an inspection of the wearable device or an update of the database(s) to create a new data sheet corresponding to the user 101 may be carried out.

Figure 2:
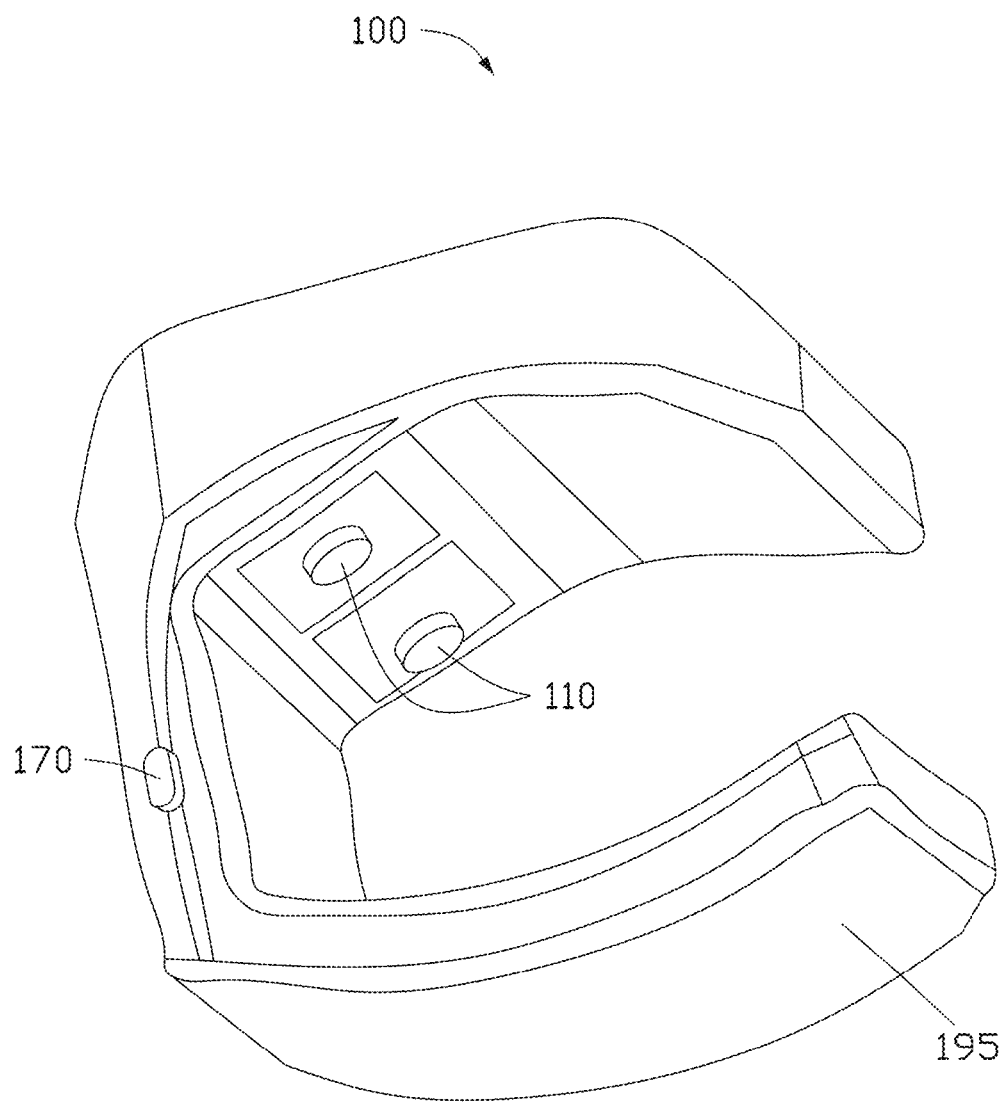
FIG. 2 is a perspective view of a wearable device of the physiological signal monitoring system in accordance with one embodiment of the present disclosure.
Figure 3:
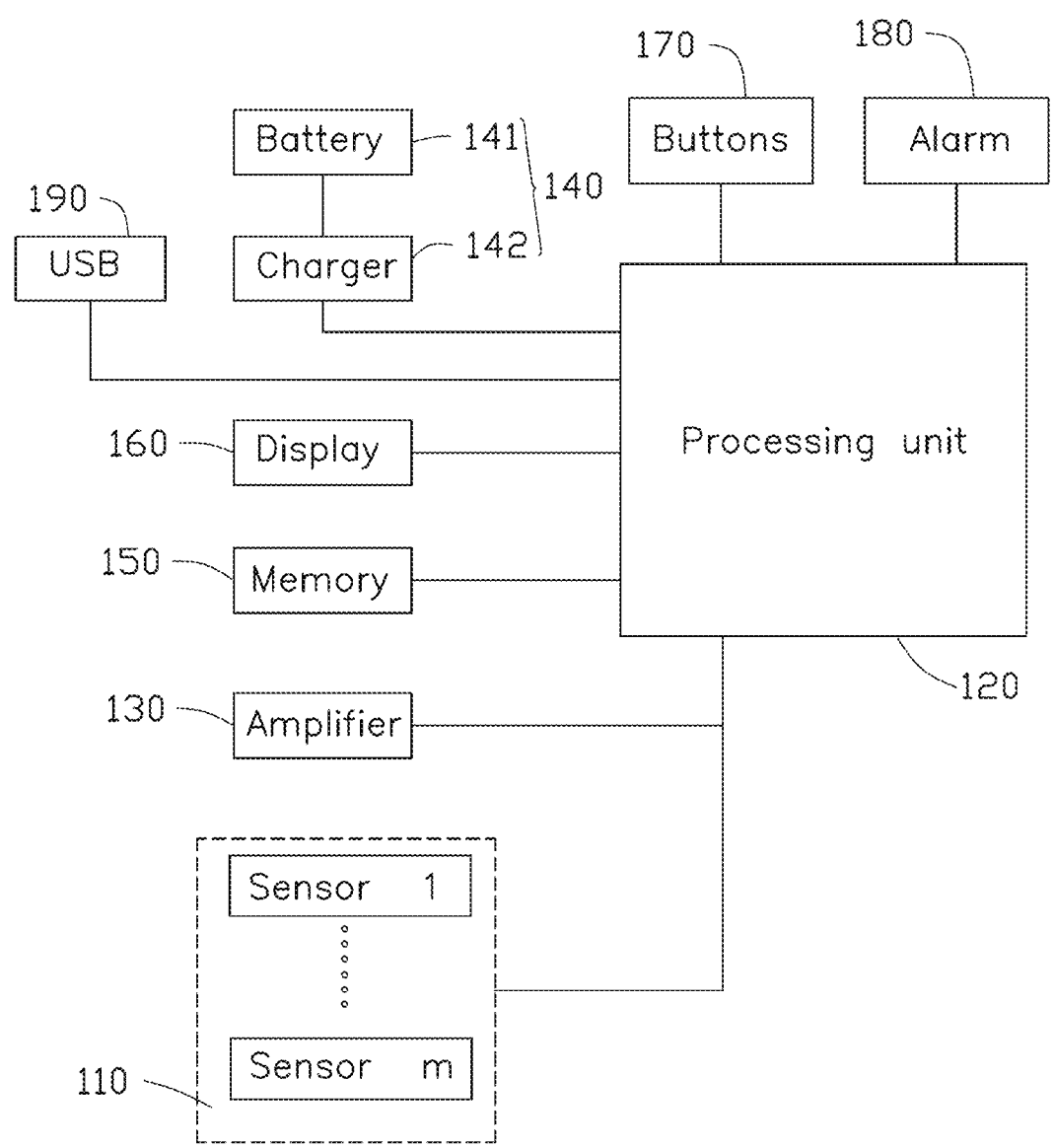
FIG. 3 is a block diagram of an overall configuration of the wearable device in accordance with one embodiment of the present disclosure.

Referring to FIG. 2 and FIG. 3. FIG. 2 depicts a perspective view of the wearable device 100 in accordance with an embodiment of the present disclosure. FIG. 3 is a block diagram depicting the overall configuration of the wearable device 100 in accordance with an embodiment of the present disclosure. The wearable device 100 may include a plurality of sensors 110, a processing unit 120, an amplifier 130, a power module 140, a memory unit 150, a display 160, a plurality of buttons 170, an alarm 180, an universal serial bus (USB) 190 and a housing 195. In the embodiment, the sensors 110 are disposed on an inner side of the wearable device 100 so as to allow direct contact of the sensors with the user's skin for sensing various types of physiological signals of the user. The processing unit 120 is electrically connected to the sensors 110, the plurality of buttons 170, the power module 140, the display 160, the memory unit 150, the USB 190, the alarm 180 and the amplifier 130. The amplifier 130 is electrically connected to the processing unit 120 and the sensors 110, and is configured to amplify the physiological signals received from the plurality of sensors 110 and transmit the amplified physiological signals to the processing unit 120. The processing unit 120 is configured to process the amplified physiological signals from the amplifier 130 and unamplified physiological signals from the sensors 110 to obtain physiological information. The processing unit 120 may also process inputs from the plurality of buttons 170. The processing unit 120 is further configured to control the display 160 and the power module 140. The power module 140 is configured to provide power to the components in the wearable device 100. The memory unit 150 is configured to store the physiological information associated with the physiological signals received from the processing unit 120. The display 160 is disposed on the housing 195 for displaying the physiological information to be read by the user 101. The display 160 may be a light-emitting diode (LED) display, a liquid-crystal display (LCD) or the like. The plurality of buttons 170 are disposed on of the housing 195 to allow the user 101 to control the wearable device 100. The USB 190 enables the wearable device 100 to be connected to one or more external devices for exporting physiological information or charging the power module 140. The alarm 180 is configured to notify a user, by for example beeping or flashing, when any abnormal physiological signal is detected. The housing 195 is configured to fully or partially accommodate the processing unit 120, the amplifier 130, the power module 140, the memory unit 150, the sensors 110, the plurality of buttons 170 and the display 160.

In at least one embodiment of the present disclosure, the processing unit 120 of the wearable device 100 may include at least one digital filter algorithm, such as infinite impulse response (UR), finite impulse response (FIR), resistor-capacitor (RC) filter, Kalman filter, extended Kalman filter, particle filter, complementary filter, fast Fourier transform (FFT), discrete cosine transform (DCT), discrete wavelet transforms (DWT), or any combination thereof, for filtering the physiological signals received from the sensors 110 in both a time domain and a frequency domain. The frequency ranges to be filtered may be set according to the signal types; for example, frequency ranging from 0.05 Hz to 300 Hz may be set for physiological signals from ECG sensors, and frequency ranging from 0.05 Hz to 10 Hz may be set for physiological signals from piezoelectric sensors. The use of the digital filter algorithm for filtering the signals in the wearable device 100 may be flexible, depending on different purposes and the signal types. For example, physiological signals from sensors, such as NPNS based sensor, NIRS based sensor, piezoelectric sensor, barometer and Doppler sensor, may be transmitted directly to the processing unit 120 without any filter circuits in between. The different frequency bands of the physiological signals may be extracted by the digital filter algorithm in the processing unit 120 for further applications, such as feature extraction or diagnosis. Therefore, the digital filter algorithm may be flexibly adjusted according to the types of the sensors 110 and applications.

As shown in FIG. 3, in at least one embodiment of the present disclosure, the power module 140 of the wearable device 100 is electrically connected to the processing unit 120 and the USB 190. The power module 140 may include a battery 141, a charger 142, a power switch (not shown), a power management unit (not shown) and a power detection unit (not shown). The battery 141 is electrically connected to the charger 142 for charging and providing power to the wearable device 100. The charger 142 is configured to be connected to an external power source via the USB 190 for charging the battery 141 and delivering a signal associated with a charging status to the processing unit 120. The power switch is configured to switch the power of the wearable device 100 on and off. The power management unit is electrically connected to the battery 141 for supplying power to the components of the wearable device 100 based on different demands. The power detection unit is electrically connected to the USB 190 for detecting a connection status of the USB 190 to the external power source. A status of the battery 141 may be displayed on the display 160. When the processing unit 120 controls the display 160 to display the charging status, the charger 142 transmits a signal of the charging status to the processing unit 120. In at least one embodiment of the present disclosure, the wearable device 100 may further include a power saving mechanism. Without the power saving mechanism, when the wearable device 100 is connected to the external power source, the charging status cannot be displayed because the wearable device 100 and the processing unit 120 are powered off. Therefore, the power detection unit may be designed to be connected to the power switch for partially powering on the wearable device 100 to enable the power saving mechanism, so that the charger 142 can transmit the signal of the charging status to the processing unit 120 for displaying by the display 160.

The physiological signal monitoring system according to various embodiments of the present disclosure as described above has the following advantages: 1. The wearable device 100 may be powered off when not in use for power conservation; 2. The wearable device 100 can be remotely shut off; 3. The display 160 can be controlled by the processing unit 120 to display multiple statuses, including battery voltage, charging status and connection status; 4. The display 160 may display the charging status when the wearable device 100 is powered off while charging: 5. The wearable device 100 may be powered off or disable unused components when being charged: 6. The wearable device 100 may remain in power or be switched off by the processing unit 120 when an external input is removed; 7. The processing unit 120 may send a visual or acoustic notification by the alarm 180 when low battery voltage is detected by the processing unit 120; 8. When low battery is detected, the processing unit 120 may execute a pre-shutdown preparation before powering off the wearable device 100 for protecting the battery 141 from over discharging, and such preparation includes saving physiological signals and physiological information in the memory 150, and sending a visual or acoustic notification by the alarm 180.

Figure 4:
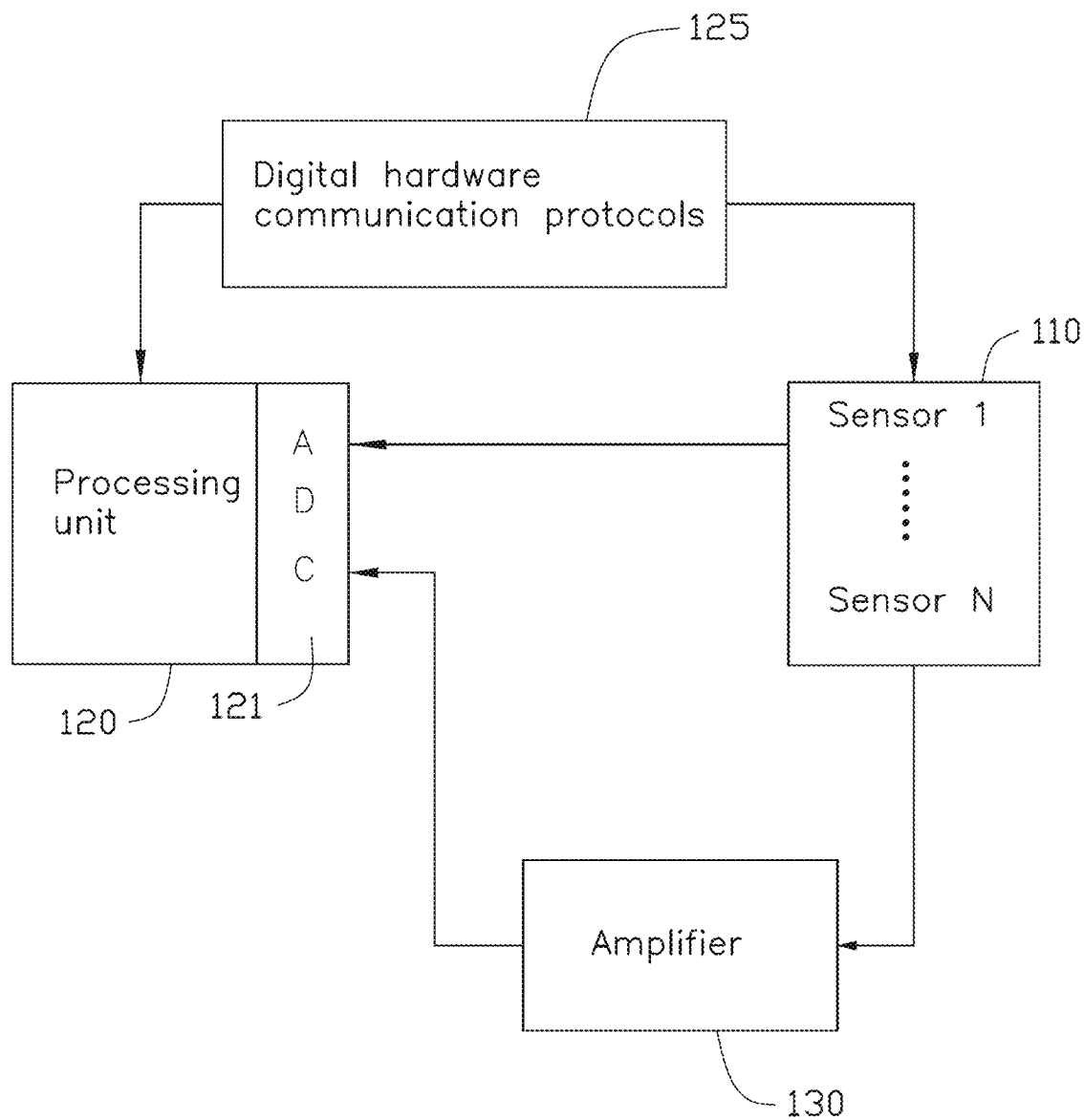
FIG. 4 is a block diagram of a configuration of the wearable device having an amplifier in accordance with one embodiment of the present disclosure.

FIG. 4 depicts a configuration of the wearable device 100 having the amplifier 130 according to one embodiment of the present disclosure. The wearable device 100 includes the processing unit 120 and the amplifier 130. The processing unit 120 may further include an analog to digital convertor (ADC) 121 configured to receive physiological signals from the sensors 110 and transmit the physiological signals to the processing unit 120. The physiological signals from the sensors 110 may be transmitted directly or via the amplifier 130 to the ADC 121, to allow the processing unit 120 to analyze the physiological signals to obtain physiological information. For example, physiological signals from a piezoelectric sensor of the sensors 110 may be amplified by the amplifier 130; in contrast, physiological signals from an optical sensor of the sensors 110 may be transmitted to the ADC 121 without amplification. Some physiological signals may be exchanged between the processing unit 120 and the sensors 110 through digital hardware communication protocols 125, such as Serial Peripheral Interface (SPI), Inter-Integrated Circuit (I²C), Controller Area Network (CAN) Bus, Universal Asynchronous Receiver-Transmitter (UART), 1-Wire® and Universal Serial Bus (USB).

Figure 5:
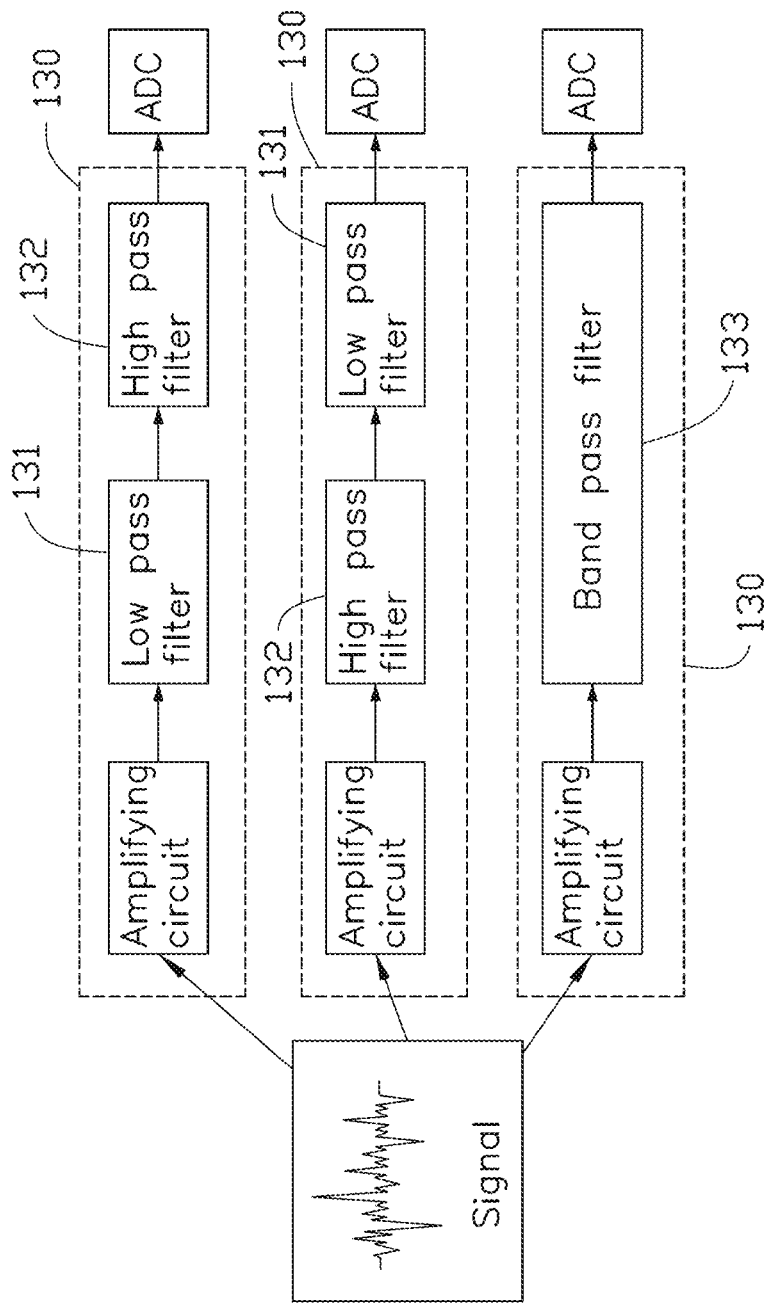
FIG. 5 is a block diagram of a configuration of one amplifier of the wearable device in accordance with one embodiment of the present disclosure.
Figure 6:
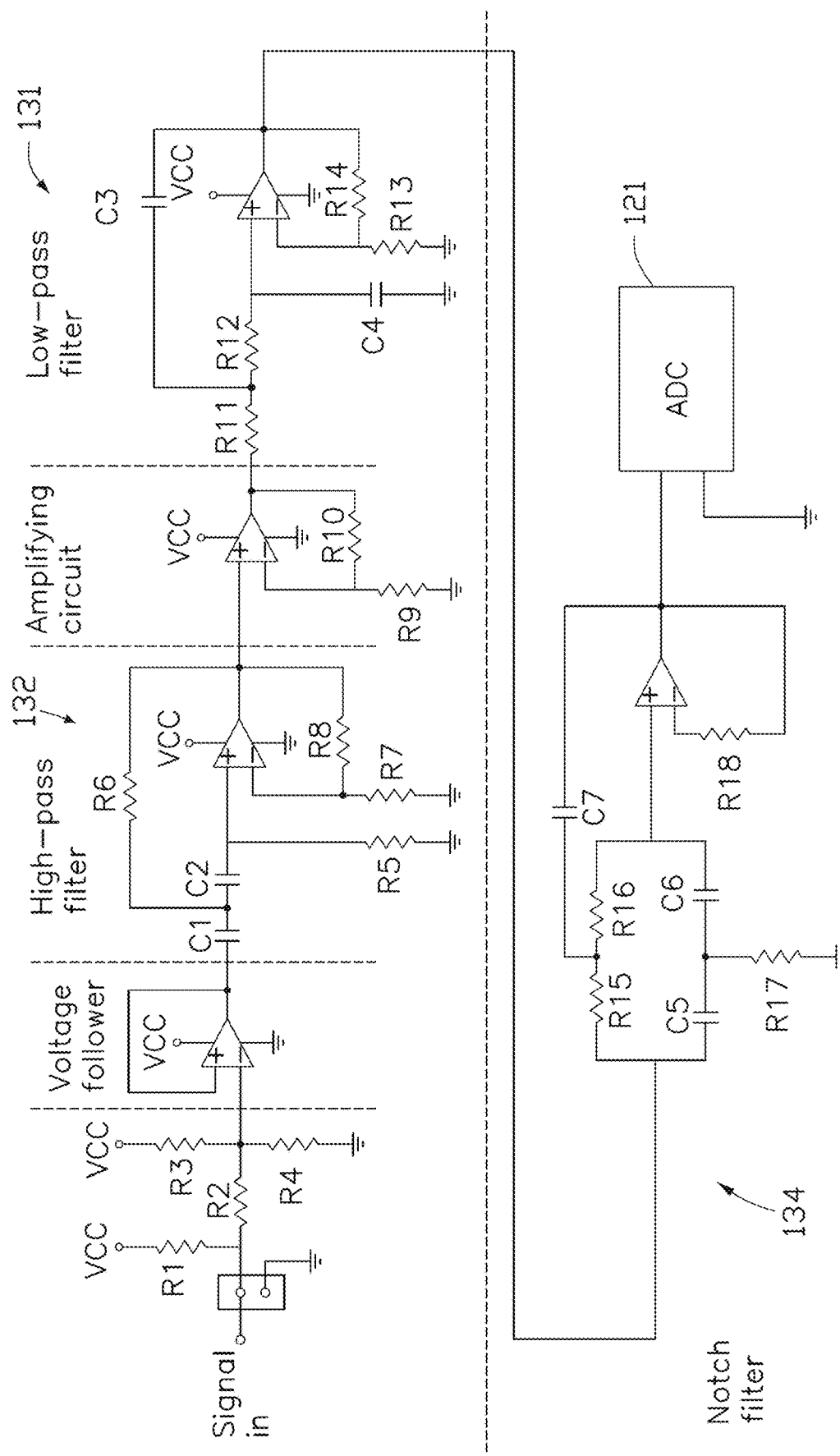
FIG. 6 is a circuit configuration of another amplifier of the wearable device in accordance with one embodiment of the present disclosure.

FIG. 5 depicts a configuration of the amplifier 130 of the wearable device 100 according to one embodiment of the present disclosure. In addition to an amplifying circuit, the amplifier 130 may also include a low pass filter 131, a high pass filter 132, a band pass filter 133, or any combination thereof. A cutoff frequency of the amplifier 130 may be configured according to types of the sensors 110, for example, a frequency range of 0.05 Hz to 500 Hz may be applied for physiological signals received from an ECG sensor; similarly, a frequency range of 0.05 Hz to 20 Hz may be applied to physiological signals in the form of mechanical waves as received from a piezoelectric sensor or a barometer. Furthermore, as shown in FIG. 6, a notch filter 134 may also be included in the amplifier 130 to suit the operational environment; the frequency of the notch filter is preferably 50 Hz or 60 Hz. In addition, a band pass filter 133 may replace a combination of the high pass filter 132 and the low pass filter 131. However, the configuration with only the band pass filter 133 may result in reception of noises outside of the desired cutoff frequency; in other words, the configuration with the combination of the high pass filter 132 and the low pass filter 131 but without the band pass filter 133 exhibits a better frequency response.

Figure 7:
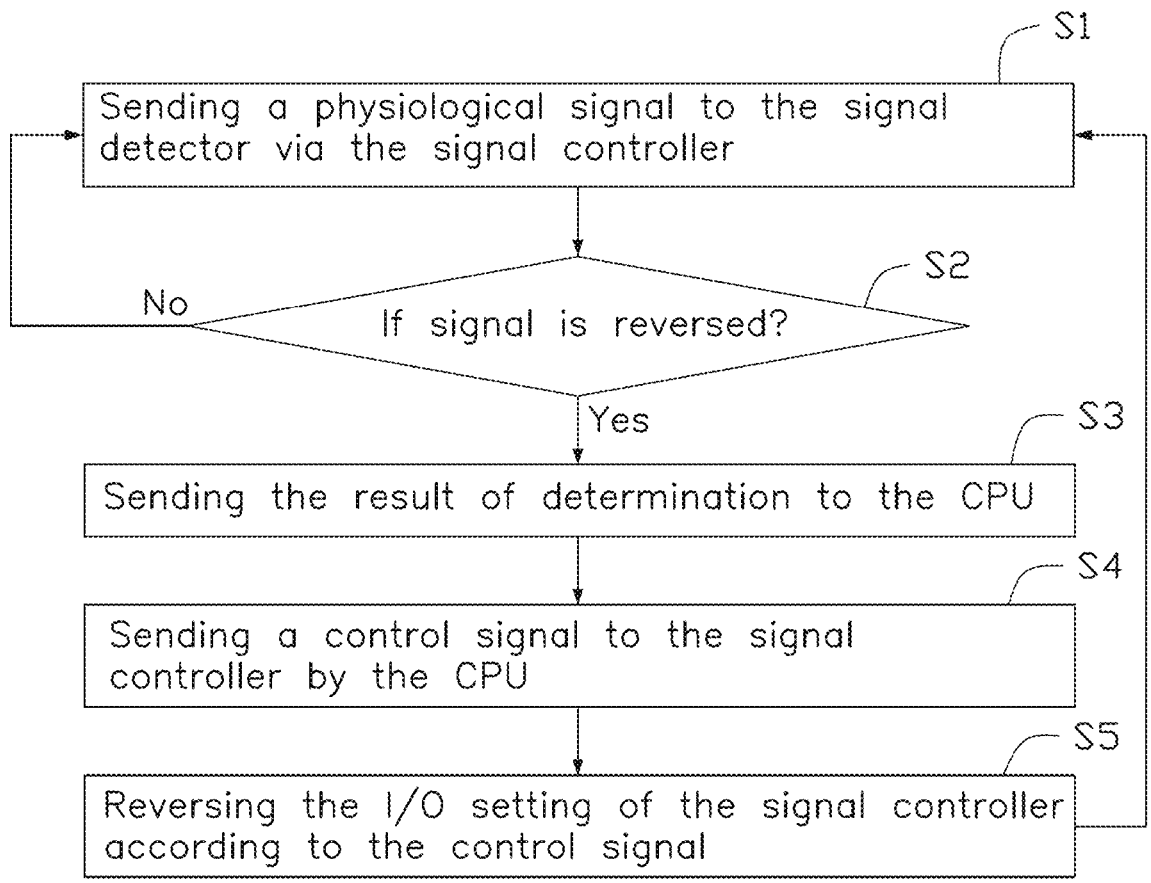
FIG. 7 is a flow diagram of an auto feedback control method of the wearable device in accordance with one embodiment of the present disclosure.
Figure 8:
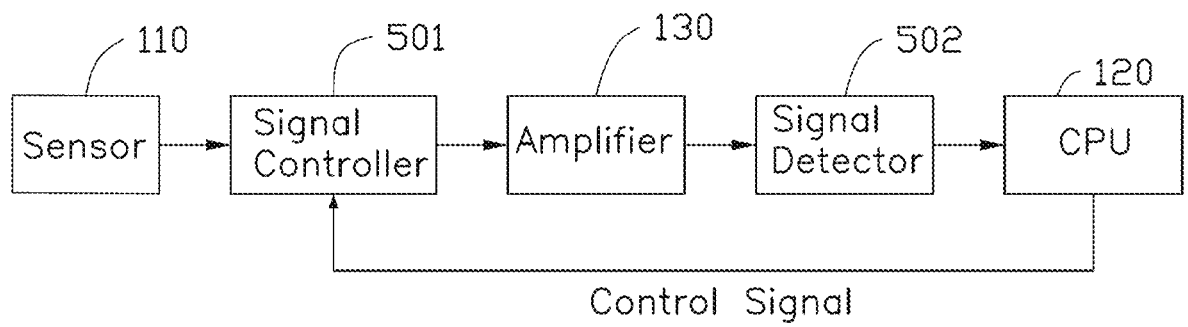
FIG. 8 is a block diagram of the wearable device including a signal controller and a signal detector in accordance with one embodiment of the present disclosure.

Referring to FIG. 7 and FIG. 8. FIG. 8 is a block diagram of the configuration of the wearable device having a signal controller and a signal detector in accordance with one embodiment of the present disclosure. FIG. 7 is a flow diagram of an auto feedback control method of the wearable device having the signal controller and the signal detector in accordance with one embodiment of the present disclosure. As shown in FIG. 8, the wearable device may further include a signal controller 501 and a signal detector 502 to enable an auto feedback control mechanism for controlling the signal direction of physiological signals received from a piezoelectric sensor of the sensors 110.

Direction of polarization in positive piezoelectric effect may vary by the direction of mechanical energy applied to a piezoelectric material, as well as by deformation and crystal lattice structure of the piezoelectric material. In addition, direction of polarization is crucial to various piezoelectric sensing applications. Therefore, in at least one embodiment of the present disclosure, an auto feedback control method may be performed by the wearable device to ensure accuracy of piezoelectric signals. As shown in FIG. 7, the auto feedback control method may include the steps of S1 to S5. In step S1, the piezoelectric sensor of the sensors 110 sends a physiological signal to the signal detector 502 via the signal controller 501 and the amplifier 130. In step S2, the signal detector 502 determines whether the signal direction of the physiological signal is reversed. If the physiological signal is reversed (i.e., the result of step S2 is yes), the auto feedback control method proceeds to step S3; otherwise, the method returns to step S1. In step S3, the signal detector 502 sends the result of step S2 to the CPU 120. In step S4, the CPU sends a control signal to the signal controller 501. In step S5, the signal controller 501 reverses an input/output (I/O) setting thereof according to the control signal, therefore changing the signal direction of one or more physiological signals subsequent to the reversed physiological signal as in step S1.

Figure 9:
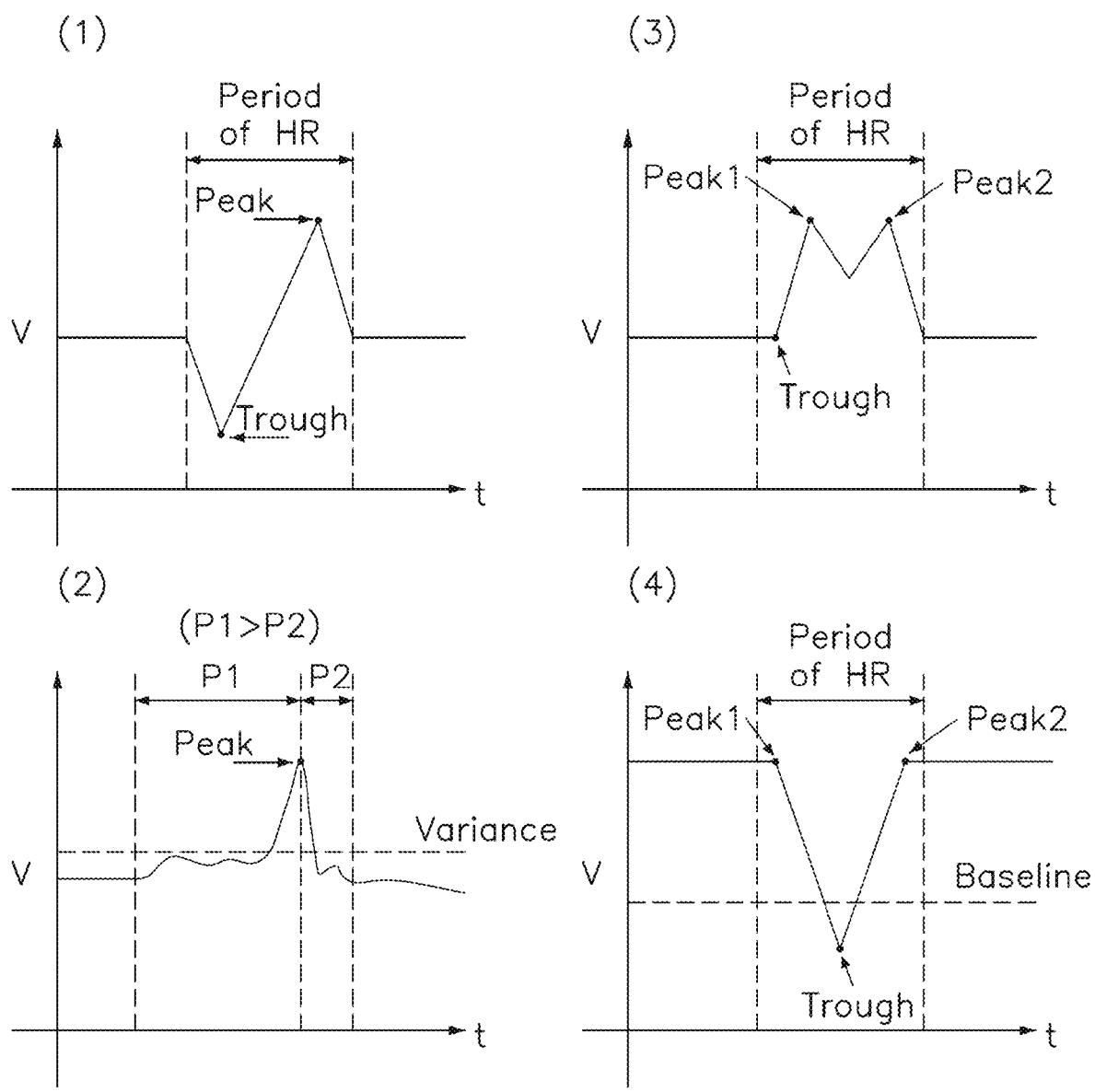
FIG. 9 is schematic illustration of characteristics and features of time domain signal representing an existence of a reversed signal in accordance with one embodiment of the present disclosure.

For the determination step in step S2, the physiological signal is determined to be reversed when the signal detector 502 detects a polarization direction of the piezoelectric sensor being opposite to an expected polarization direction (that is, when the presence of a reversed signal being detected). More specifically, the signal detector 502 may utilize characteristics and features of the physiological signal in time domain and/or frequency domain from the signal controller 501, in order to determine the signal direction of the physiological signal. The signal direction may represent the polarization direction of the piezoelectric sensor. FIG. 9 exemplifies the characteristics and features of time domain signals that represent the presence of a reversed signal.

Figure 10:
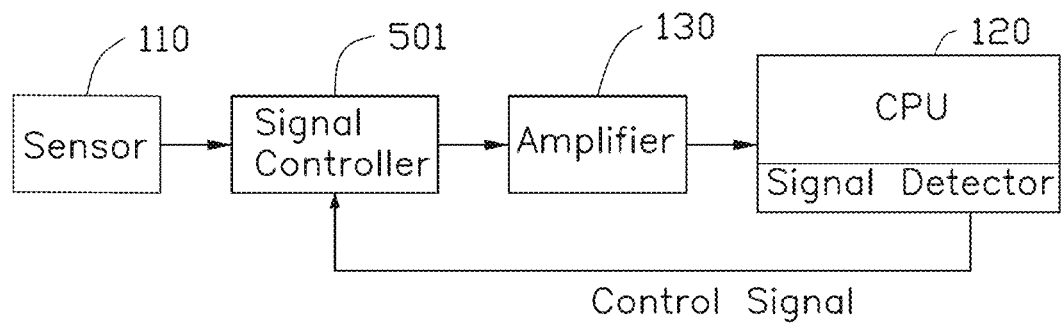
FIG. 10 is a block diagram of a configuration of the wearable device having the signal controller and an integrated signal detector in accordance with one embodiment of the present disclosure.

Referring to FIG. 10, a configuration of the wearable device having the signal controller 501 and an integrated signal detector in accordance with one embodiment of the present disclosure is provided. The signal detector 502 may include an integrated circuit (IC; not shown) with processing capability or an equivalent detection circuit (not shown) in replace of the IC. The detection circuit may be a comparator, a logic processing circuit, or a field programmable gate array (FPGA) with logic coded by register transfer language (RTL). As shown in FIG. 10, the signal detector 502 may also be so integrated into the CPU 120 that the signal detector 502 is realized in the form of a software or algorithm for performing the steps S1-S3. In one embodiment of the present disclosure, the signal controller 501 may be a software controlled electronic logic gate or electronic circuits with logic structure. The signal controller 501 is connected to the electrodes of the piezoelectric sensor, and configured to send the physiological signals received from the piezoelectric sensor to the signal detector 502. At the same time, the signal controller 501 is also configured to receive the control signal from the CPU 120 and change the direction of the physiological signal output.

Figure 11:
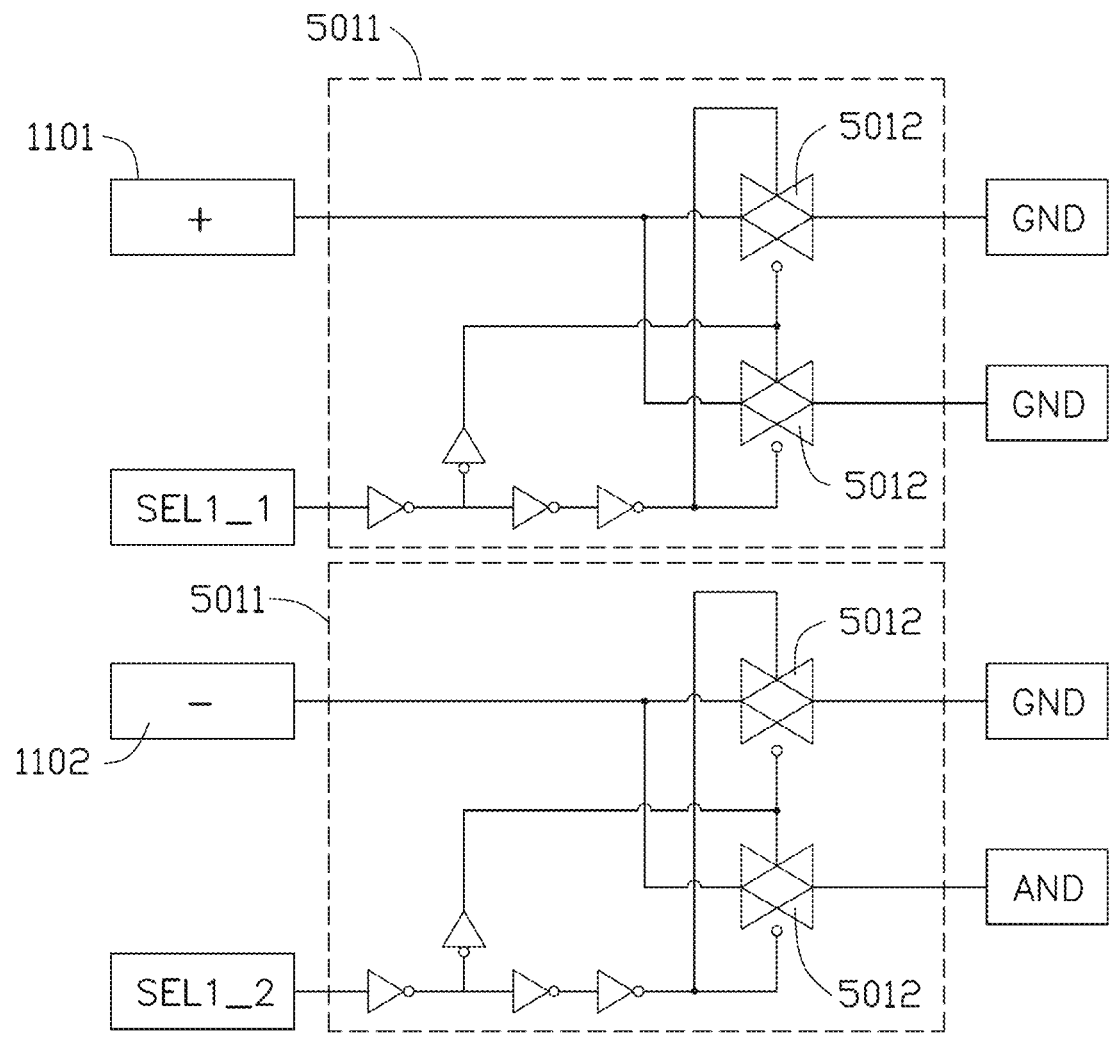
FIG. 11 is a circuit diagram of the signal controller of the wearable device in accordance with one embodiment of the present disclosure.

Referring to FIG. 11, a circuit layout of the signal controller of the wearable device in accordance with one embodiment of the present disclosure is provided. As shown in FIG. 11, the control circuit may include two control TCs 5011 and a plurality of logic gates 5012 in each of the control ICs 5011; the plurality of logic gates 5012 may be configured to have Boolean logic control capability. One of the control ICs 5011 is connected a positive electrode 1101 of the piezoelectric sensor of the sensors 110, whereas the other control ICs 5011 is connected to a negative electrode of the piezoelectric sensor of the sensors 110. In some embodiments, the control ICs 5011 may be a microcontroller (MCU) or the like with processing capabilities identical or comparable to the plurality of logic gates 5012. The control ICs 5011 are configured to control the I/O setting of the signal controller 501 by the plurality of logic gates 5012. Thus, the signal direction the physiological signal sent to the CPU is changed according to the I/O of the signal controller 501. In one embodiment of the present disclosure, the signal controller 501 with processing capabilities may be configured to determine by itself whether to adjust the I/O setting, or to passively receive the control signal from the signal detector 502 to adjust the I/O setting.

Figure 12:
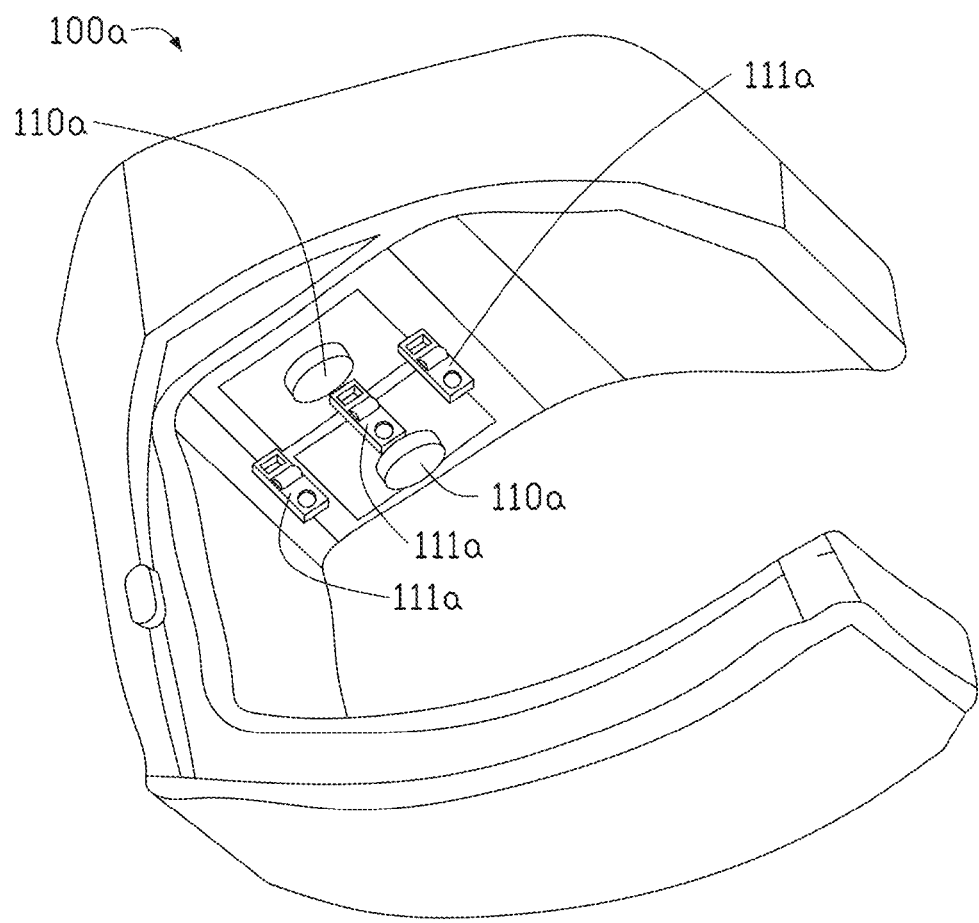
FIG. 12 is a perspective view of a wearable device in accordance with one embodiment of the present disclosure.

Referring to FIG. 12, a perspective view of a wearable device according to one embodiment of the present disclosure is provided. The wearable device 100a may be worn on a wrist or a calf. The wearable device 100a includes a plurality of major sensors 110a disposed on the inner side of the wearable device 100a and capable of detecting radial artery pulse beats. For example, the major sensors may be NPNS based sensors, NIRS based sensors, piezoelectric sensors, barometers, Doppler sensors, and/or laser diode and photodiode sensors. may be The combination and the quantity of the major sensors 110a may be chosen based on different demands.

As shown in FIG. 12, in at least one embodiment of the present disclosure, the wearable device 100a may further include a plurality of auxiliary sensors 111a. The plurality of auxiliary sensors 111a may be disposed adjacent to the major sensors 110a for aligning the major sensors 110a to a position of an artery of the user. For example, a position of the wearable device 100a may be detected by utilizing NIRS, laser or photodiode as the auxiliary sensors 111a to measure blood oxygen level of the artery, to determine if the major sensors 110a are positioned around the artery or a vein. Accordingly, the wearable device 100a may send a notification by an alarm to prompt the user to align the wearable device 100a to the artery, so that the major sensors 110a are placed at an optimal position for receiving mechanical waves of pulse beats generated by the artery.

The auxiliary sensors 111a may also be configured to detect the content in the artery. The combination and the quantity of the auxiliary sensors 111a are not limited to the aforementioned. In another embodiment of the present disclosure, the wearable device 100a may include two major sensors 110*a* and one auxiliary sensor 111*a*. The major sensors 110*a* may be two piezoelectric sensors, and the auxiliary sensor 111*a* may be an optical sensor positioned between the two piezoelectric sensors. The two piezoelectric sensors and the optical sensor may form a straight line, and the auxiliary sensor 111*a* may be disposed around the artery to allow the processing unit 120 to determine whether the major sensors 110*a* are right above an artery. Alternatively, the auxiliary sensor 111*a* may be placed on one side of the major sensors 110*a*, instead of in between the major sensors 111*a*; however, the major sensors 110*a* and the auxiliary sensor 111*a* still have to be arranged linearly to form a straight line. In another embodiment, the wearable device may include two major sensors but without an auxiliary sensor. The two major sensors may be two optical sensors or a combination of optical sensor and piezoelectric sensor. In the case of two optical sensors, a correction function would be required for PTT determination, due to the deviating nature of PTT measured by optical sensor.

Figure 13:
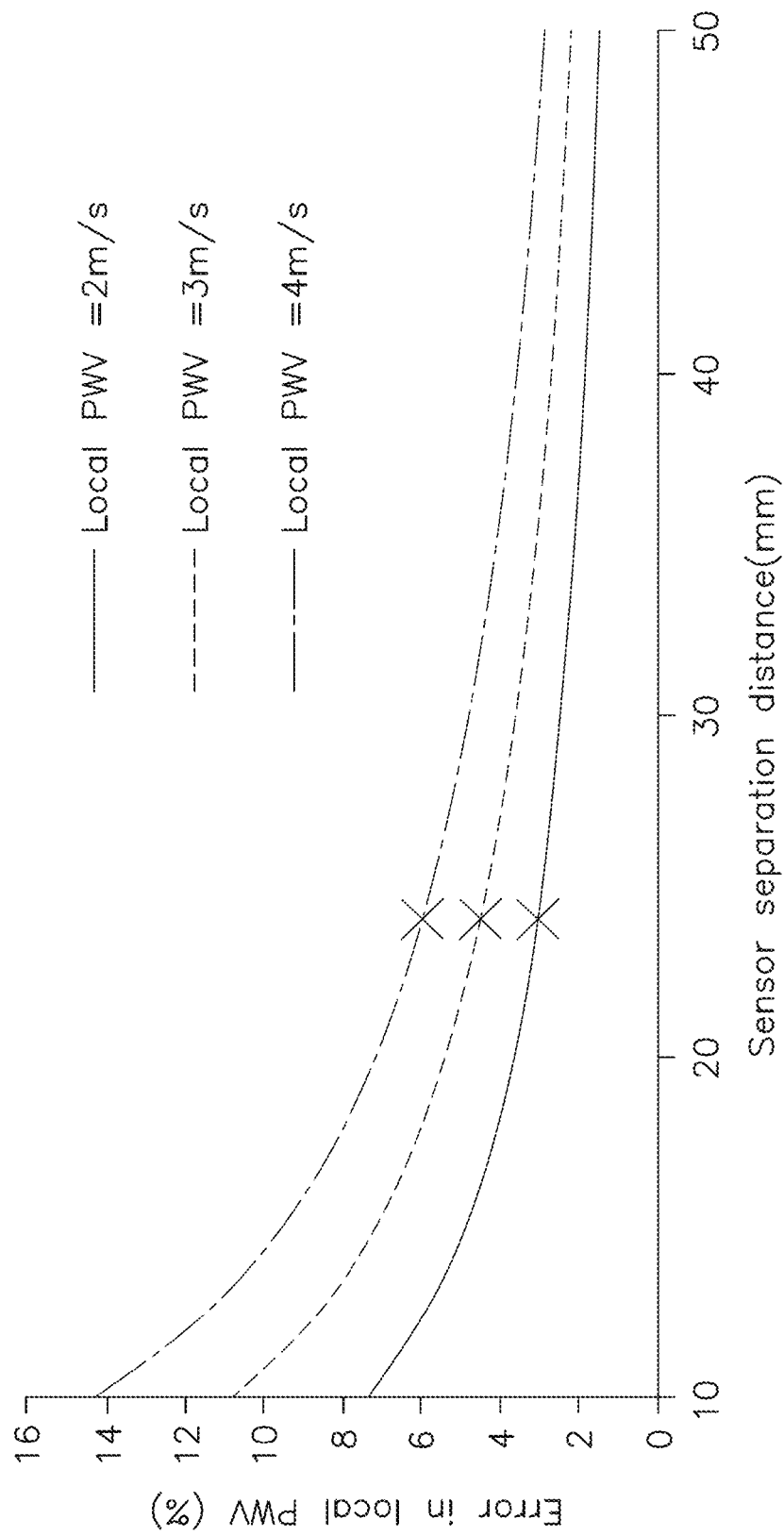
FIG. 13 is a schematic diagram of a relationship between pulse wave velocity measurement error and sensor separation distance in accordance with one embodiment of the present disclosure.

As shown in FIG. 13, different degrees of error may occur in pulse transit time (PTT) measurements due to different pulse wave velocity (PWV) and different physical distance between the sensors. When the distance between the sensors remains constant, the measurement error for high PWV may be larger than that for low PWV; when the PWV remains constant, the measurement error for short distance between the sensors may be larger than that for long distance.

Figure 14:
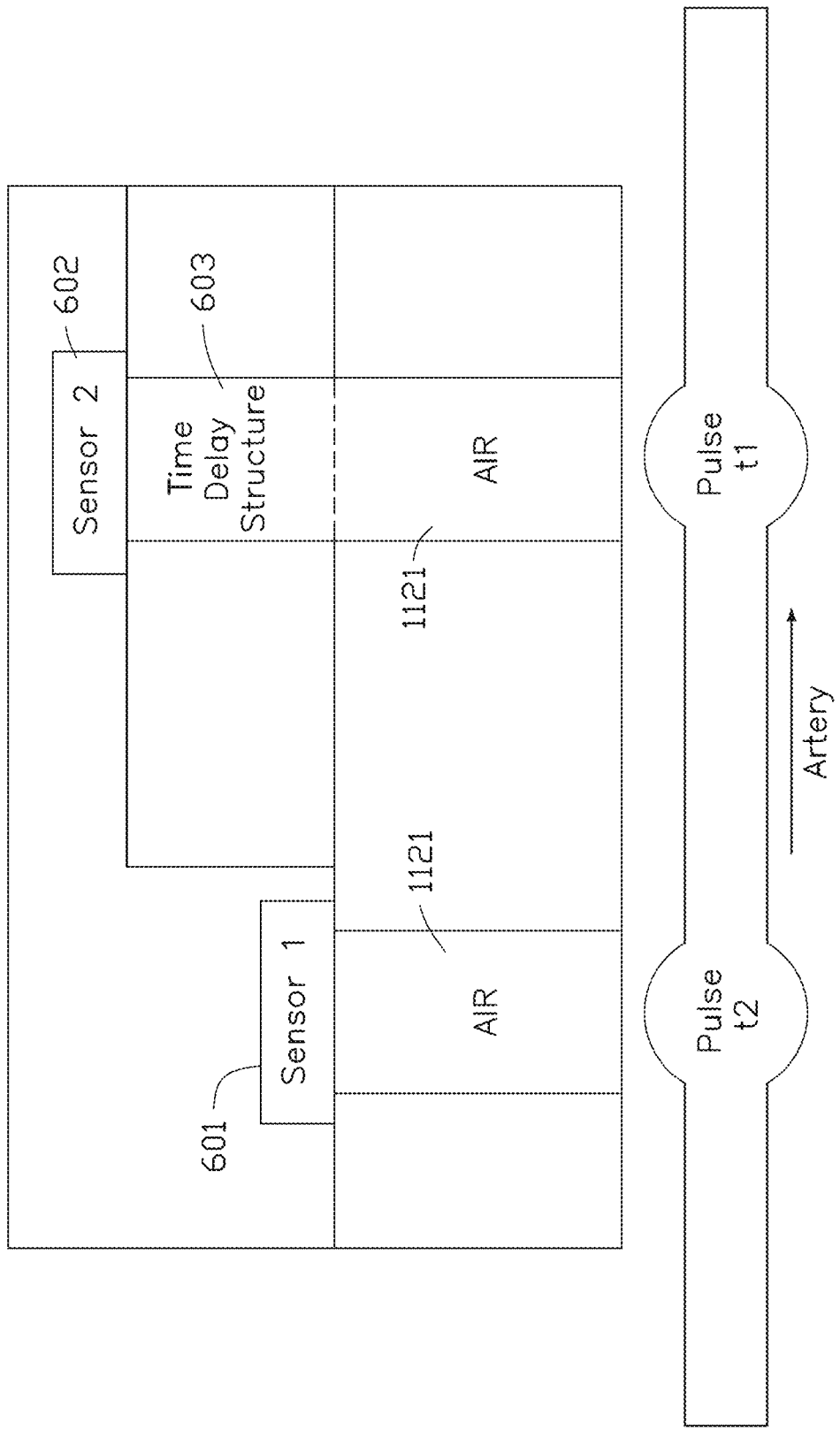
FIG. 14 is a schematic cross-sectional view of the wearable device having a time delay structure in accordance with one embodiment of the present disclosure.

Referring to FIG. 14, a cross-sectional view of the wearable device having a time delay structure in accordance with one embodiment of the present disclosure is provided. In order to reduce the distance between the sensors for miniaturization without increasing the measurement errors, the wearable device may further include a time delay structure 603 for lengthen the travel distance of mechanical waves in air. As shown in FIG. 14, for PTT determination between a first sensor 601 and a second sensor 602, the time delay structure 603 may be connected to the second sensor 602 to lengthen a path distance between a measurement point of a pulse t1 and the second sensor 602. Hence, $PTT=t_1-t_2$ becomes $PTT=t_1(\alpha \times V+b)-t_2$, which realizes a delaying effect of PTT. Therefore, measurement errors caused by insufficient distance between the first sensor 601 and the second sensor 602 is reduced.

In addition, PTT can be determined by the processing unit 120 according to a known path distance of the time delay structure 603 and characteristics of the mechanical waves travelling in the time delay structure 603. In another embodiment, a calibration function $\alpha \times V+b$ may be obtained by comparing measurements of the wearable device having the time delay structure 603 to measurements of the wearable device without the time delay structure 603. Therefore, the PTT may be determined as the processing unit 120 runs the calibration function.

Figure 15:
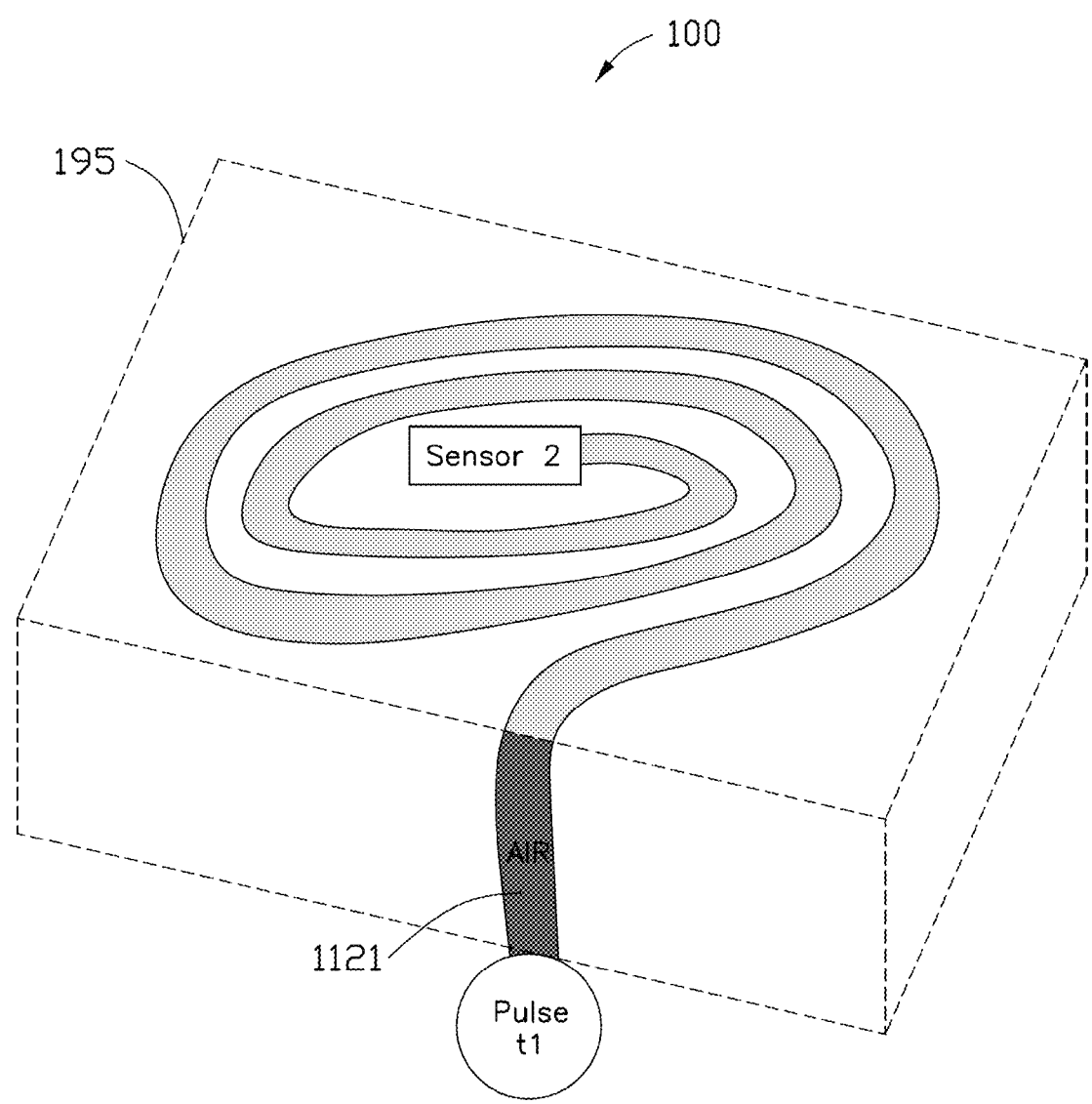
FIG. 15 is a schematic perspective through view of the wearable device having the time delay structure in a shape of Archimedes spiral in accordance with one embodiment of the present disclosure.

Furthermore, in order to integrate the time delay structure 603 into a wearable device without significantly increasing the overall size of the wearable device 100, the time delay structure 603 may have a shape of an Archimedes spiral, as illustrated in FIG. 15. The Archimedes spiral may be disposed in the housing 195 of the wearable device 100, wherein the spiral and the sensor 2 are on a plane substantially perpendicular to a through-hole 1121. In some embodiments, the time delay structure 603 may have a zig-zag shape (not shown) or any shape that lengthens the path distance while being compact in space. Furthermore, the time delay structure may be a tube having a medium for transmitting mechanical waves. The medium may be a gas (such as air), a gel like material, or a soft matter, otherwise, the time delay structure may be made of a solid material that is capable of mechanical wave transmission.

Figure 16:
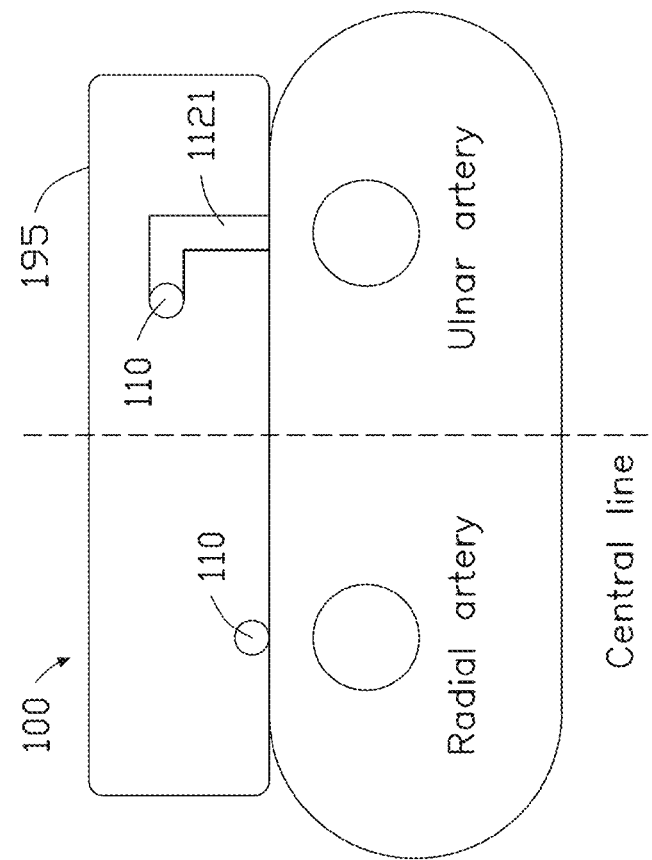
FIG. 16 is a schematic illustration of sensor placement of the wearable device in accordance with one embodiment of the present disclosure.
Figure 16:
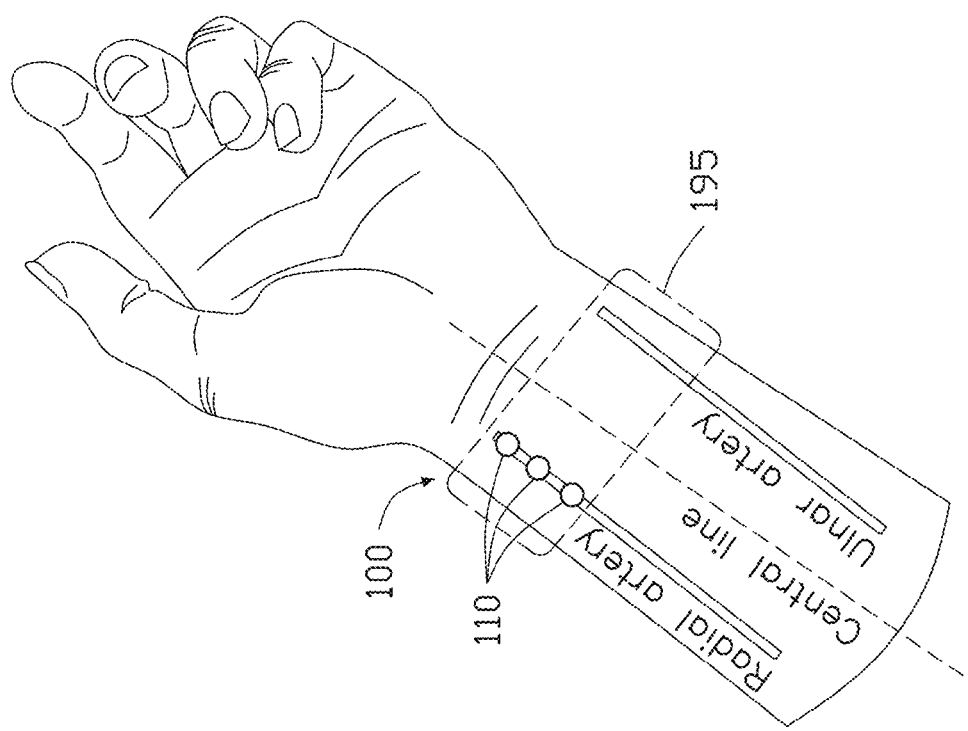

Referring to FIG. 16. In one embodiment of the present disclosure, the sensors 110 in the wearable device 100 may include a mechanical wave sensor and an optical sensor. The mechanical wave sensor may be a piezoelectric sensor, a barometer, a surface acoustic wave sensor, a vibration sensor, or the like. The optical sensor may be a near infrared sensor, a magneto-optic sensor, a laser-Doppler sensor, or the like. The placement of the sensors 110 is crucial for measurement accuracy and user comfort. As shown in FIG. 16 on the right, the housing 195 may include a plurality of through-holes 1121 that form passages between the sensors 110 and a skin surface, and hence enable signal transmission between an artery and the sensors 110. Alternatively, as shown in FIG. 16 on the left, the sensors 110 may be disposed on the surface of the housing 195 to contact the user's skin surface directly. In this case, the sensors 110 should be placed directly above a radial artery or an ulnar artery, and at least two of the sensors 110 should form a substantially straight line parallel to the direction of the radial artery or the ulnar artery. On the other hand, if the sensors 110 are disposed in the housing 195 of the wearable device, at least two of the through-holes 1121 have to form a substantially straight line parallel to the direction of the radial artery or the ulnar artery. For ergonomic purposes, as exemplified in FIG. 16, the through-holes 1121 may be disposed closer to one side than the other of the wearable device 100; in other words, the through-holes 1121 may be so disposed that they do not overlap with a central line of wearable device 100. Similarly, if the sensors 110 are disposed on the surface of the wearable device, the sensors 110 may be disposed asymmetrically to the central line of the wearable device; that is, being closer to one side than the other of the wearable device.

Figure 17:
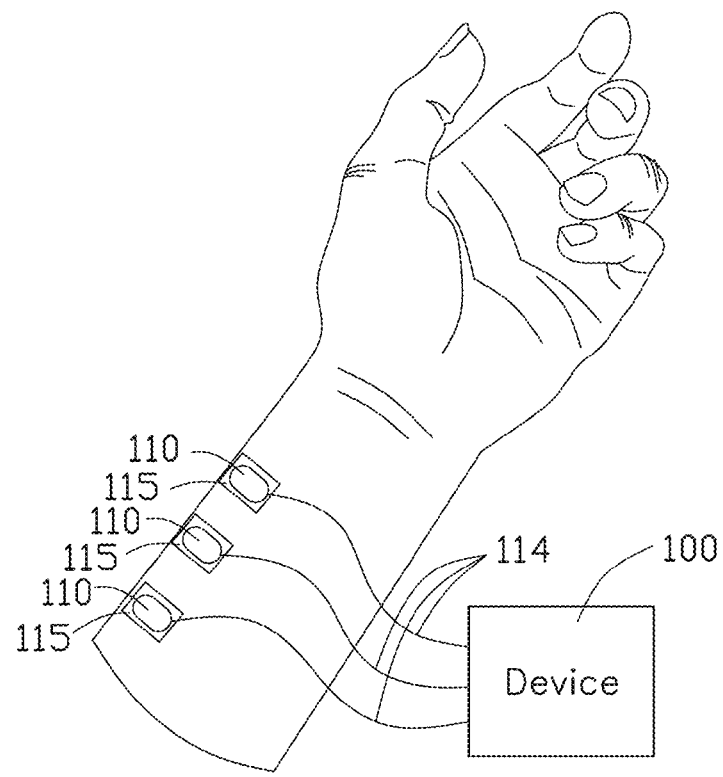
FIG. 17 is a schematic illustration of the wearable device having external sensors in accordance with one embodiment of the present disclosure.
Figure 18:
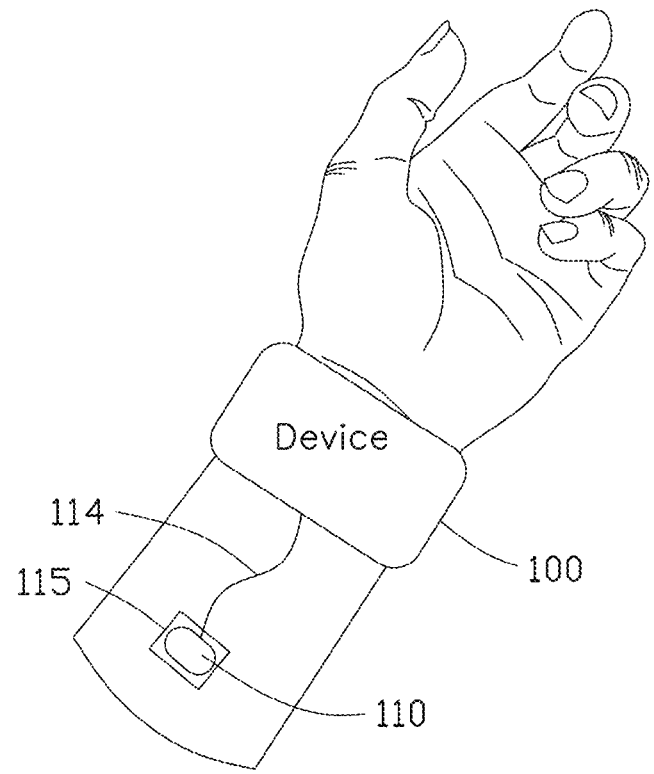
FIG. 18 is a schematic illustration of the wearable device having an external sensor in accordance with one embodiment of the present disclosure.

Referring to FIG. 17 and FIG. 18, in one embodiment of the present disclosure, the wearable device 100 may include externally disposed sensors 110 outside of the housing. As illustrated in FIG. 17, each of the sensors 110 may be connected to the wearable device 100 externally by a cable 114, and the sensors 110 may be removably attached around an artery of a user by adhesive patches 115, to allow measurement of at least one physiological signal from the user. Therefore, at least one physiological signal measured by the sensors 110 may be transmitted to the wearable device 100 via the cable 114 for determining at least one physiological information. In another embodiment as illustrated in FIG. 18, the wearable device 100 includes one external sensor 110 with all of the other sensors (not shown) being internal sensors in the housing. The external sensors 110 may be connected to the wearable device 100 by a cable 114 and removably attached to a user by an adhesive patch 115; in this case, the processing unit (not shown) in the wearable device 100 utilize physiological signals received from both of the external and internal sensors 110 to determine at least one physiological information. It should be noted that, the type and quantity of the external sensors 110 is not limited to the aforementioned. It should also be noted that, the sensors 110 may also be wirelessly connected to the wearable device 100.

Figure 19:
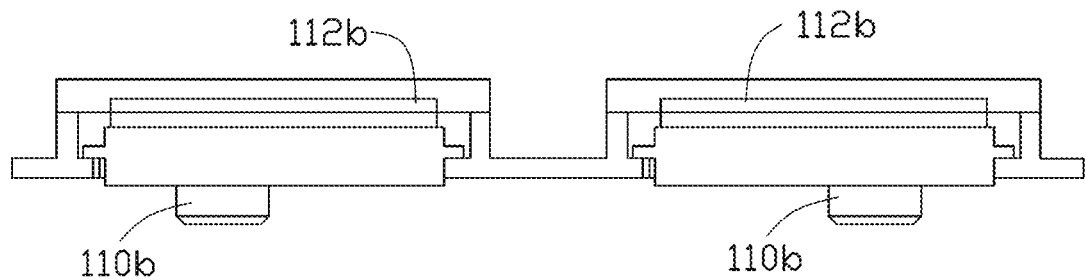
FIG. 19 is a schematic cross-sectional view of an auxiliary structure of the wearable device in accordance with one embodiment of the present disclosure.

Referring to FIG. 19, the auxiliary structure according to an embodiment of the present disclosure is provided. As exemplified in FIG. 19, the auxiliary structure 112*b* may be disposed under the major sensors 110*b*. The auxiliary structure 112*b* may include an elastic material acting as a buffer for absorbing shocks and filtering unwanted signals. The elastic material of the auxiliary structure 112b may be a spring, a foaming material or the like, and directly contact the user's skin.

Figure 20:
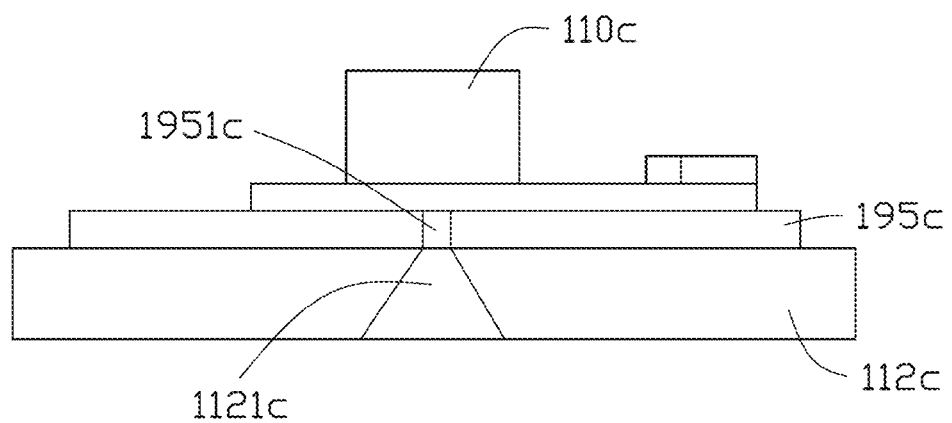
FIG. 20 is a schematic cross-sectional view of the wearable device having another auxiliary structure in accordance with one embodiment of the present disclosure.

Referring to FIG. 20, a wearable device having another auxiliary structure 112c and at least one major sensors 110c according to an embodiment of the present disclosure is provided. For major sensors of the wearable device that receive mechanical wave signals via air transmission, improving structure of the through-hole may enhance the sensitivity of the major sensors, by for example, adjusting the diameter of the through-hole to increase pressure of the mechanical wave signal. In at least one embodiment of the present disclosure, the major sensors 110c may include one or more barometers. The barometers are accommodated in the housing 195c (only partially illustrated). The auxiliary structure 112c is disposed on an external surface of the housing 195c corresponding to the positions of the barometers. The auxiliary structure 112c may be a layer of silicone rubber, which include one or more through-holes 1121c located corresponding to a central position of the major sensors 110c. The through-hole 1121c may be conical shaped with two open ends, one end of which having a smaller diameter is connected to the housing 195c, and the other end of which having a larger diameter is in direct contact with the user's skin. The housing 195c may include one or more cylindrical pin-holes 1951c disposed corresponding to the smaller open end of the through-hole 1121c. The conical shaped through-holes 1121c are configured to enhance reception of mechanical wave signals and sensitivity of the major sensors 110c.

Figure 21:
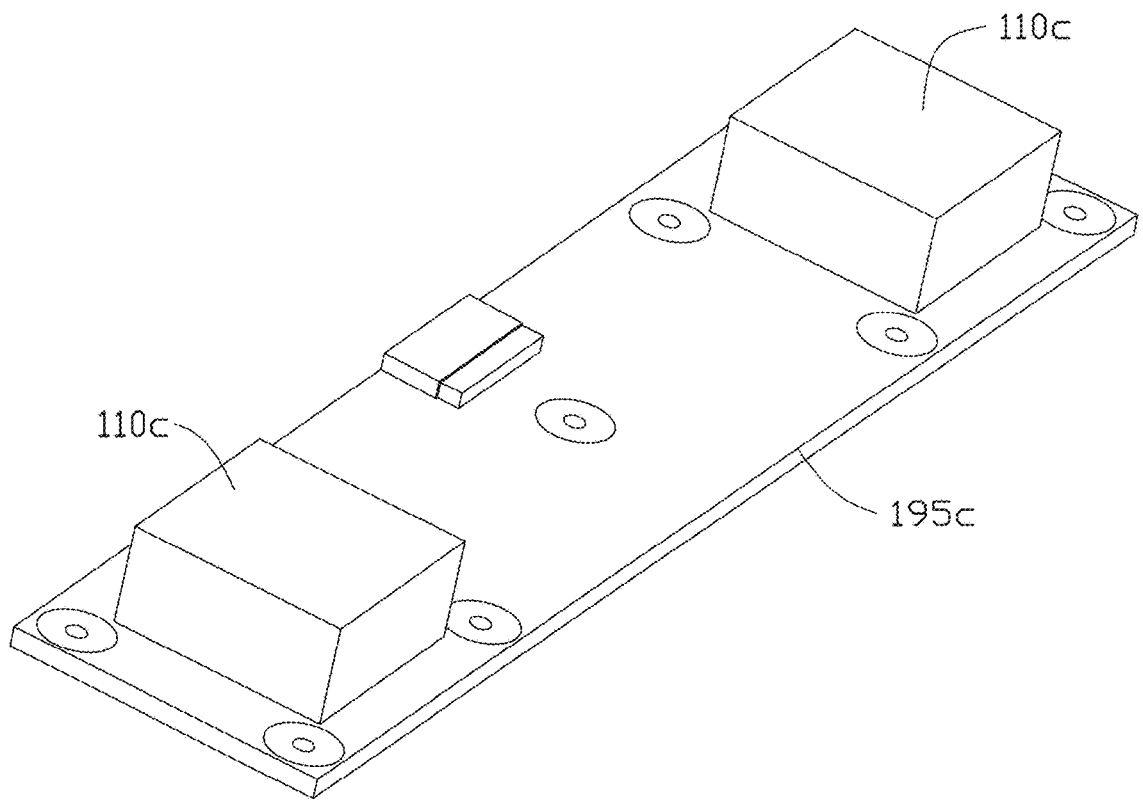
FIG. 21 is a perspective view of a wearable device having a barometer array in accordance with one embodiment of the present disclosure.

Referring to FIG. 21. In an embodiment, the auxiliary structure 112c of the wearable device may also be integrated as part of the housing 195c. As shown in FIG. 21, the wearable device may include a barometer array composed of a plurality of barometers 110c. The configuration and the quantity of the barometers are not limited the aforementioned.

Figure 22:
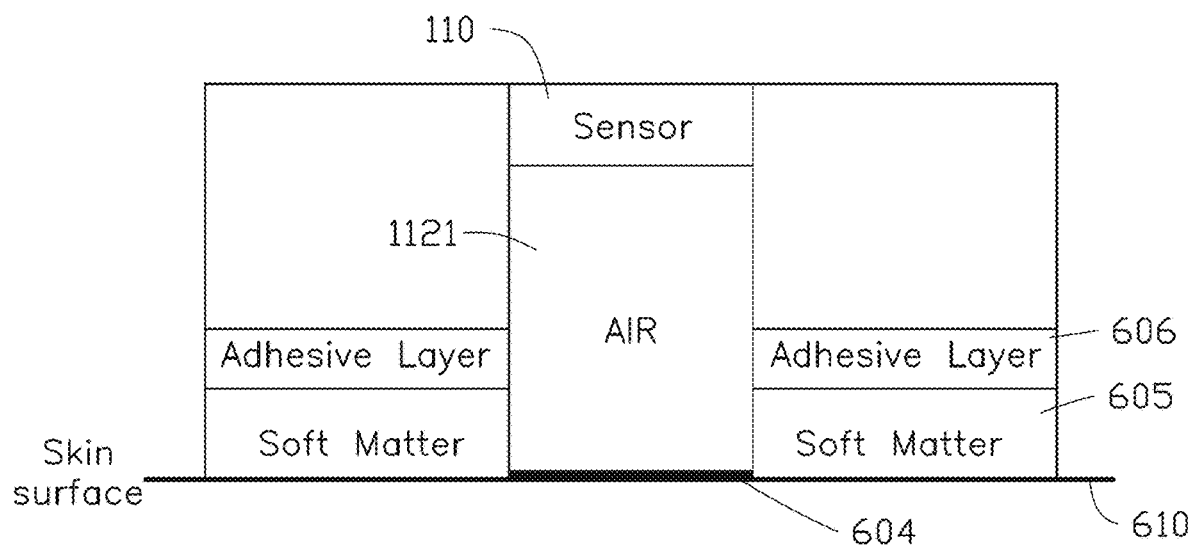
FIG. 22 is a schematic cross-sectional view of the wearable device having a contacting material in accordance with one embodiment of the present disclosure.
Figure 23:
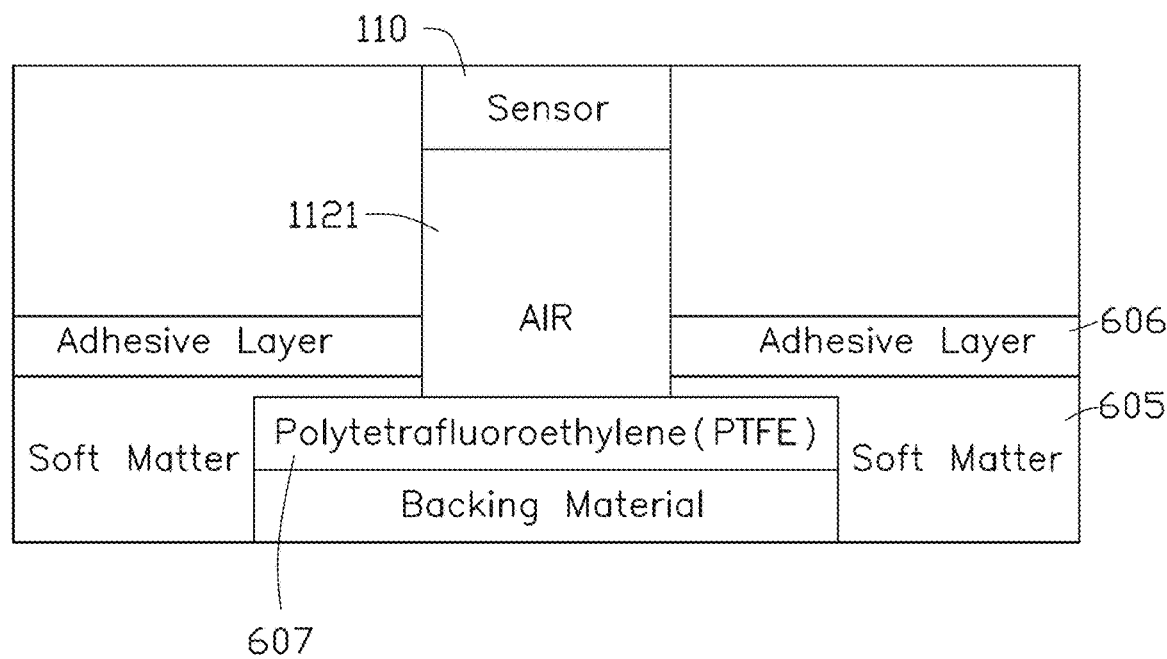
FIG. 23 is a schematic cross-sectional view of the wearable device including a mesh material in accordance with one embodiment of the present disclosure.
Figure 24:
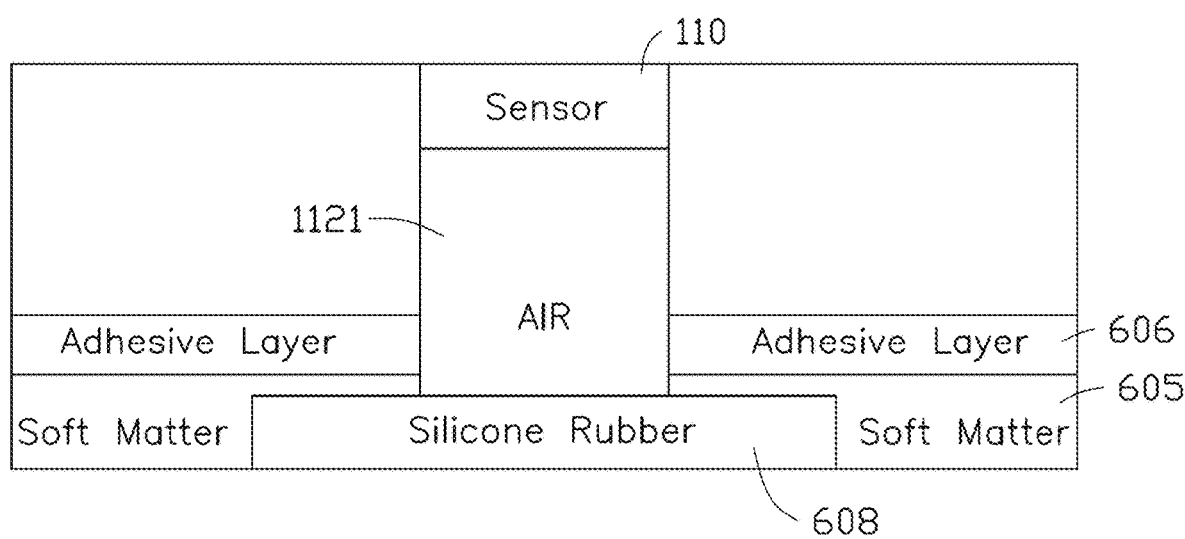
FIG. 24 is a schematic cross-sectional view of the wearable device including a film in accordance with one embodiment of the present disclosure.

Referring to FIG. 22, FIG. 23, and FIG. 24. Increasing seal tightness between the through-hole 1121 and skin surface 610 may result in stronger signal strength. As shown in FIG. 22, the seal tightness may be enhanced by a contacting material 605, which may be a soft matter disposed around an opening 604 of the through-hole 1121 and attached to the wearable device 100 by an adhesive layer 606. In addition, as shown in FIG. 23, to prevent foreign objects (such as liquid or dirt) from entering the through-hole, a mesh material 607 may be used to cover the through-holes; the mesh material 607 may be made of polytetrafluoroethylene (PTFE). In one embodiment of the present disclosure, a backing material may be fixed to the mesh material 607 to support the mesh material 607. Furthermore, as shown in FIG. 24, a silicone rubber film 608 may be used in replace of the mesh material 607 to achieve the same function.

Figure 25:
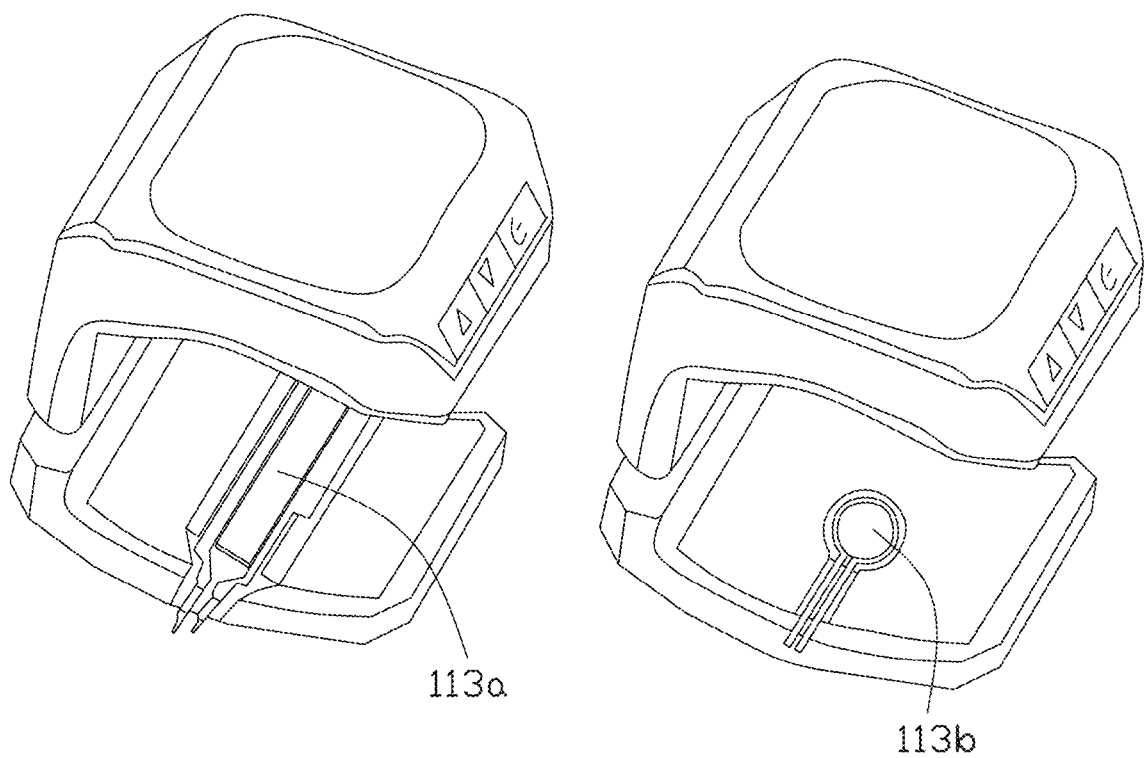
FIG. 25 is a perspective view of the wearable device having a stress sensing structure in accordance with one embodiment of the present disclosure.

Referring to FIG. 25, a stress sensing structure of a wearable device according to an embodiment of the present disclosure is provided. The wearable device is designed to be clipped on the wrist or the calf of the user with slight pressure to cause deformation of the artery. In order to compensate errors caused by artery deformation, piezoelectric sensors 113a and 113b that has high linearity are disposed on opposite sides of the major sensors (not shown) and the auxiliary sensors (not shown). The piezoelectric sensors 113a and 113b are configured to sense and determine the pressing strength against the user 101 to determine a level of calibration for the physiological signals from the major sensors and the auxiliary sensors. The level of calibration is determined by the processing unit based on stress, flow velocity and/or amplitude statistical model. The configuration and the quantity of the piezoelectric sensors are not limited to the aforementioned.

In at least one embodiment of the present disclosure, the wearable device 100 may be fixed to a user by straps, therefore causing a surface pressure ($P_1$) to be applied to the user. Signals for pulse transit time (PTT) measurements, $P_1$ and a mechanical wave amplitude (Amp) may be obtained by using a strain gauge sensor of the sensors 110. As a sensor area of the strain gauge sensor, a mechanical wave transmission space, and a transmitting medium remains unchanged, a relationship among $P_1$, Amp, and pulse pressure ($P_0$) may be represented by Amp=a $P_1$b+c $P_0$d. Therefore, the $P_1$ and Amp from the strain gauge sensor may be analyzed by a processing unit 120 to determine $P_0$. However, the relationship among $P_1$, Amp, and $P_0$ may be linear or non-linear, and thus may be calibrated through empirical data of $P_1$, Amp, and $P_0$.

In one embodiment of the present disclosure, the sensors 110 may include an accelerometer and a gyroscope. The accelerometer has great long-term stability but lack instantaneous sensitivity, whereas the gyroscope has great sensitivity for instantaneous change in angular velocity. In an embodiment of the present disclosure, Kalman filter, extended Kalman filter, particle filter or complementary filter, may be adopted by the processing unit 120 to fuse the signals from the two sensors. Therefore, the processing unit 120 may use the signals obtained by the gyroscope to correct the signals obtained by the accelerometer to obtain a precise three-dimensional transformation of the wearable device 100. Step count of the user 101 may be determined based on a periodical transformation occurring in any of the XYZ axial dimensions of the fused signals. In addition, each user has different walking habits, so the acquired three-dimensional transformation may also be considered as a sub-collection for determining user's identity.

According to Poiseuille's law, the power of four of blood vessel diameter is inversely proportional to pulse wave velocity (PWV). Therefore, in an embodiment of the present disclosure, the sensors 110 may include a force-sensitive resistor disposed on one side of the wearable device 100 and in direct contact with the user's forearm for enabling statistical analysis of the relation of pound per square inch (PSI) to the PWV to be performed by the processing unit 120, and hence obtaining a PSI calibration coefficient. Therefore, the PWV may be calibrated by the PSI calibration coefficient by the processing unit 120.

Figure 26:
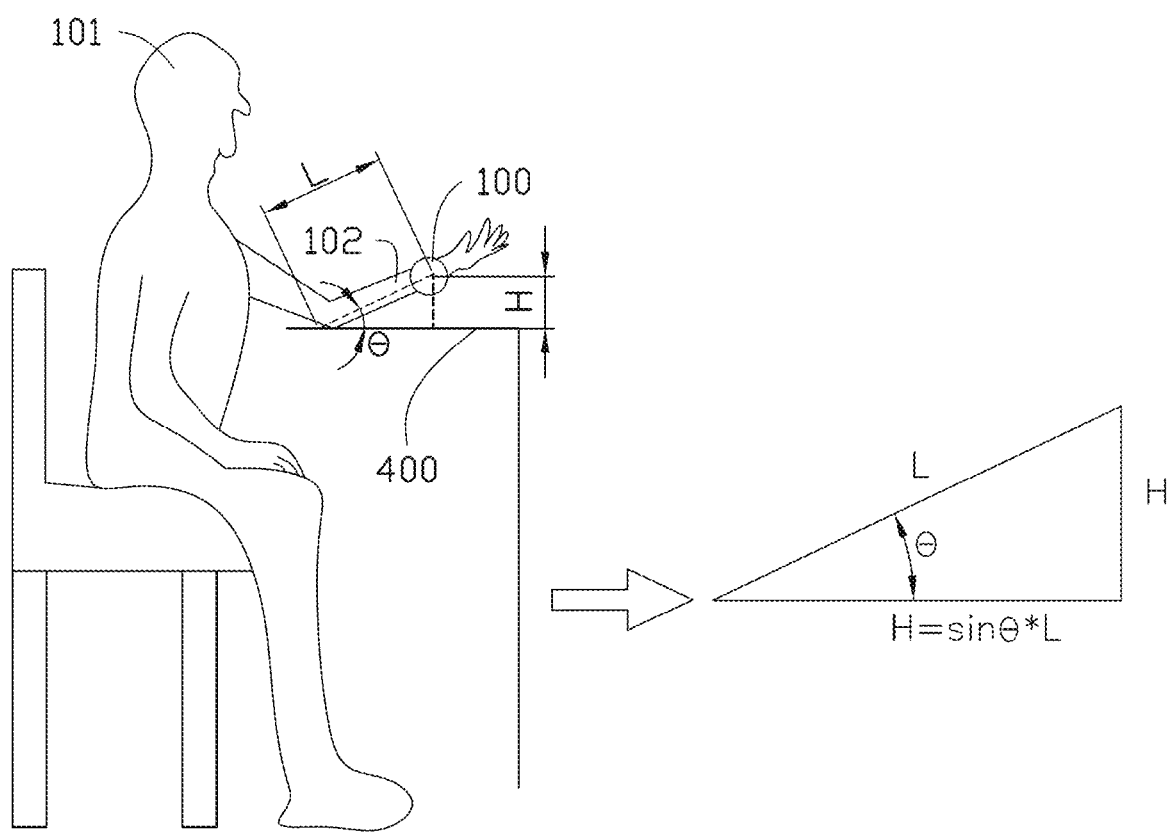
FIG. 26 is a schematic illustration showing a mathematic relationship among a height, a forearm length, and an angle between the wearable device and the horizontal plane in accordance with one embodiment of the present disclosure.

Referring to FIG. 26. In at least one embodiment of the present disclosure, blood pressure of the user may be determined based on hemorheology and hemodynamics. Therefore, a height of fluid flow according to Bernoulli's principle and the blood vessel diameter according to Poiseuille's law may be utilized to calibrate a pulse wave velocity (PWV), so as to compensate a height (H) between the wearable device 100 and a horizontal plane 400. As illustrated in FIG. 26, determination of the height H is based on the function L×sin θ=H, wherein L is a length of a forearm 102, and θ is an angle between the forearm 102 and the horizontal plane 400. The angle θ in any axial direction (such as x, y, z) may be obtained through at least one of the sensors, such as an accelerometer or a gyroscope. The length L of the forearm 102 may be inputted by the user 101, or may be determined based on a height to arm ratio of the user 101. The sensors 110 may also include ultrasound, laser time-of-flight, LED time-of-flight or Doppler radar, to detect the distance between the wearable device 100 and the elbow of the user 101 to obtain the length L.

The height H may be determined by the processing unit 120. In another embodiment of the present disclosure, the height H may be obtained by one of the sensors, such as ultrasound, laser time-of-flight, LED time-of-flight or Doppler radars, that directly detects the height H between the wearable device 100 and the horizontal plane 400. Since blood is a non-Newtonian fluid, a correction coefficient obtained from experimental statistics is needed for calibrating the relation between the height H and the PWV. When the angle θ and the height H are close to zero, the forearm 102 of the user 101 may be determined as nearly parallel to the horizontal plane 400; for example, when the user 101 wears the wearable device 100 during sleep or when the forearm 102 is laid down flat with the wearable device 100.

For calibration of the pulse wave velocity (PWV), a "Posture-PWV" look up table may be created by obtaining correction coefficients corresponding to different angles and angular acceleration received from the accelerometer and the gyroscope. Therefore, blood pressure measurement under any posture may be performed by referencing the "Posture-PWV" look up table stored in the processing unit 120. The posture is determined by the processing unit 120 according to any axial (such as x, y, z) changes detected by the accelerometer and gyroscope. Accordingly, the PWV or pulse transit time may be adjusted based on the axial changes. In addition, any other similar posture recognition sensors, such as a vibration sensor, may also be utilized.

Figure 27:
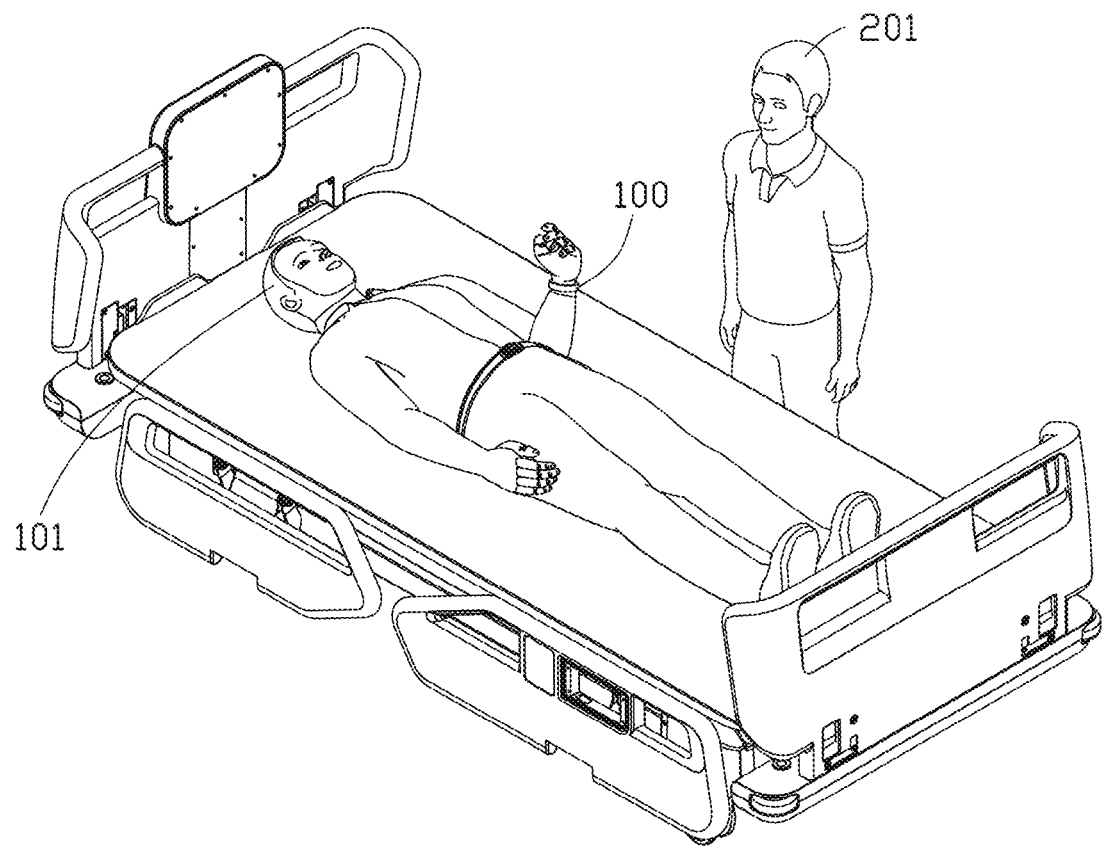
FIG. 27 a schematic illustration of a forearm of a user subjecting to blood pressure measurement in accordance with one embodiment of the present disclosure.

Referring to FIG. 27. In a 24-hour monitoring mode, the wearable device 100 may determine the posture of the user 101 by the integrated accelerometer and gyroscope when the forearm 102 is lifted as exemplified in FIG. 27. When the posture of the user as determined by the processing unit 120 of the wearable device 100 according to the axial changes lasts for a period of time longer than a threshold, the wearable device 100 may enter a measuring mode, and display a systolic blood pressure (DBP) and a diastolic blood pressure (DBP) of the user. The posture is determined by any axial changes measured by the accelerometer and the gyroscope. Any other similar posture recognition sensors, such as a vibration sensor, may also be used.

Figure 28:
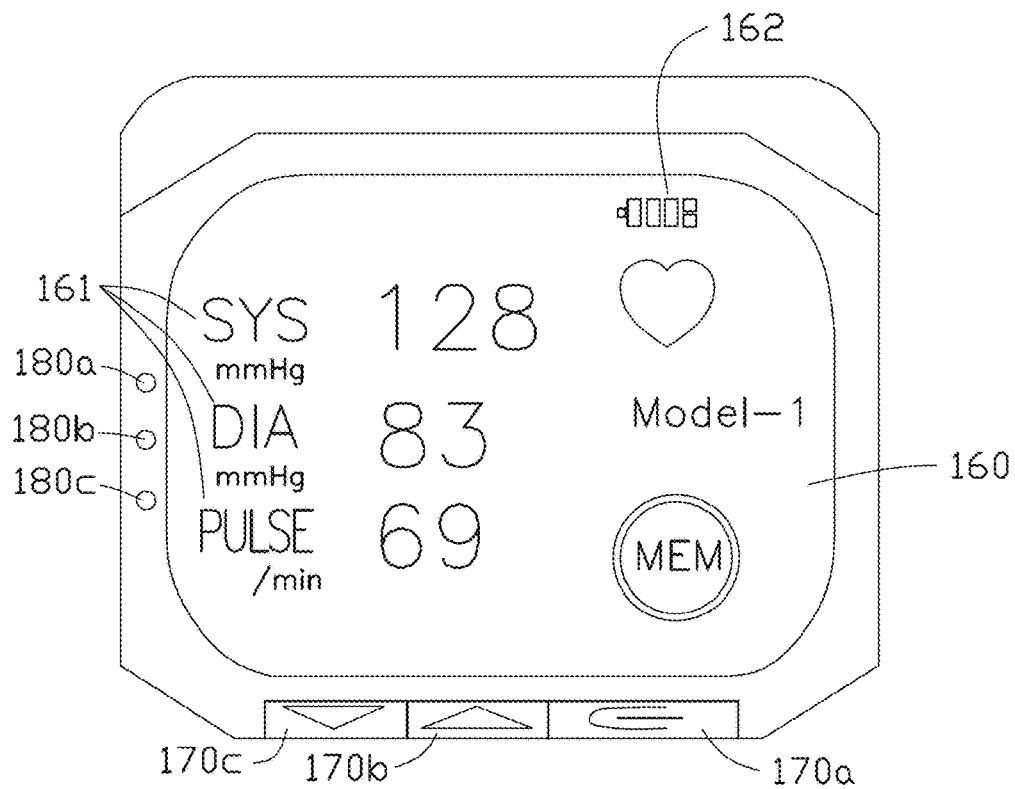
FIG. 28 is a schematic illustration of a user interface of the wearable device in accordance with one embodiment of the present disclosure.

Referring to FIG. 28, a user interface of the wearable device according to an embodiment of the present disclosure is illustrated. The user interface may include a display 160, a plurality of control buttons 170a, 170b, 170c and a plurality of indicators 180a, 180b, 180c. The display 160 may display multiple physiological statuses 161 and battery status 162. The plurality of control buttons may include a power button 170a, a page up button 170b and a page down button 170c.

Figure 29:
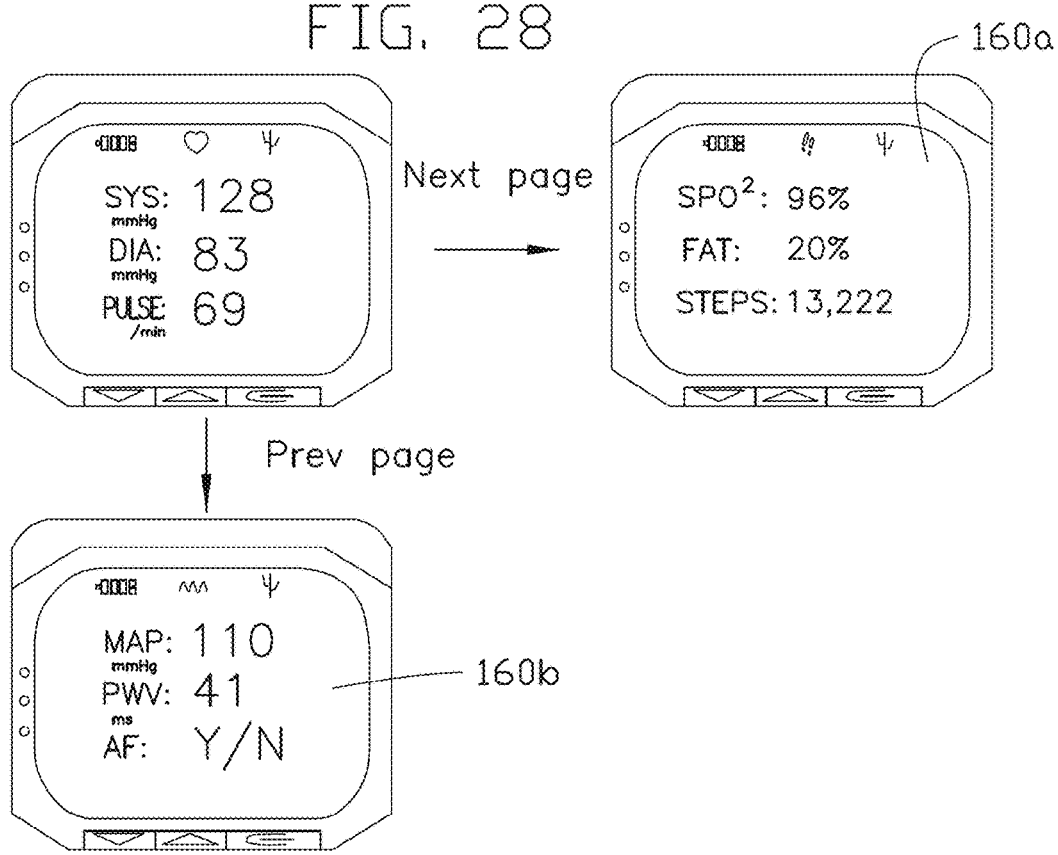
FIG. 29 is a schematic illustration of page views on a display of the wearable device in accordance with one embodiment of the present disclosure.

Referring to FIG. 29, the pages on the display of the wearable device to present various physiological signals according to an embodiment of the present disclosure are illustrated. As shown in FIG. 29, the page down button 170c may be configured to flip the page to a next page 160a when being pressed. Similarly, the page up button 170b may be configured to flip the page to the previous page 160b when being pressed. When the page up button 170b and the page down button 170c are pressed simultaneously for a period of time, the display 160 may switch to display history data, including for example physiological information determined previously. The plurality of indicators may include a power indicator 180a, an alarm indicator 180b and a processing status indicator 180c; the indicators may be composed of different color lighting elements, such as LEDs or the like.

The power indicator 180a may be configured to illuminate when the processing unit detects low battery voltage. The alarm indicator 180b may be configured to illuminate when an abnormal physiological status is detected by the processing unit. The processing status indicator 180c may be configured to illuminate when the processing unit is operating.

In at least one embodiment of the present disclosure, the sensors 110 may include a least one of NPNS, NIRS, piezoelectric sensor, barometer, Doppler sensor, ultrasound transducer, laser diode and photodiode for obtaining physiological signals associated with pulse arrival time (PAT), pulse transit time (PTT), pulse wave velocity (PWV), pulse beat, irregular pulse peak (IPP), irregular heart beat (IHB), atrial fibrillation (AF), heart rate variability (HRV) and heart rate, based on multiple arterial pulse beats or multiple readings of the same pulse from different sensors. The PWV may be determined by the processing unit 120 based on the equation PWV=Δd/Δt(PTT), wherein the Δt (PTT) represents pulse transit time (PTT) caused by Windkessel effect. The PTT is determined from multiple waveforms of the same pulse detected by at least two of the sensors 110 with a known distance (Δd) between the sensors 110. The PTT may be measured between any two points in proximity to a human artery, and the two points may be 0.5 cm to 15 cm apart from each other. Moens-Korteweg (MK) function $$PWV = \sqrt{\frac{hE}{dp}},$$

wherein E is Young's modulus, h is a thickness of blood vessel wall, d is diameter of blood vessel and ρ is blood density, may be utilized to determine the PWV of a long straight elastic tube. By substituting Young's modulus equation $E=E_o e^{\alpha P}$ into the MK function, the MK function may be rewritten as $$PWV = \sqrt{\frac{hE_0 \exp^{(\alpha P)}}{dp}},$$

The relationship between the PWV and the intra-arterial pressure (P) is ln(PWV)=P(Linear relate); therefore, a regression calibration of ln(PWV)=P(Linear relate) may be performed by inputting massive laboratory data into $$P = a \, \ln\left(\frac{b}{PTT^2}\right)$$

wherein $$b = \frac{\rho \times d \times x^3}{E \times h} \text{ and } x^2 = \Delta d = \text{length of artery}.$$

Consequently, the intra-arterial pressure (P) may be determined by the processing unit 120 by utilizing the MK function and at least one hemodynamic parameter obtained from the blood vessel wall thickness (h), blood vessel diameter (d) and blood density (ρ). It should be noted that, the hemodynamic parameter may also include blood vessel stiffness, artery expansion, Young's modulus of blood vessel, etc.

Realistically, human arteries are not ideal elastic tubes. In order to obtain a more precise result of the intra-arterial pressure (P), indirect measurements of the blood vessel wall thickness (h), the blood vessel diameter (d), and the blood density (ρ) are performed by the sensors 110 and subjected to massive laboratory data modelling. Therefore, additional calibrations may be performed during the determination of the intra-arterial pressure (P) by the processing unit 120. The relationship between systolic blood pressure (SBP), diastolic blood pressure (DBP) and mean arterial pressure (MAP) is $$MAP \simeq \frac{2}{3}(DBP) + \frac{1}{3}(SBP).$$

The quicker the heartbeat, the closer the mean arterial pressure (MAP) gets to the average of the systolic blood pressure (SBP) and the diastolic blood pressure (DBP) as described by $$MAP \simeq DBP + 0.01 \times e^{\left(4.14\frac{40.74}{HR}\right)}(SBP - DBP),$$

which also describes that the artery shape may vary with increasing pressure. Therefore, SBP, DBP and MAP may be determined by P. In addition, the pulse beats acquired over a measurement unit time (e.g., 10 seconds or 30 seconds) by the sensors 110 may be used to determine irregular pulse peak (IPP), irregular heart beat (IHB), atrial fibrillation (AF) and heart rate variability (HRV) by the processing unit 120. Firstly, time differences between consecutive pulse beats are determined and averaged; secondly, deviations of each time difference from the averaged time difference are determined; and finally, an IPP is determined when any deviation exceeds a threshold (e.g., 15%, 20% or 25%). Furthermore, irregular heart beat (IHB) may be determined when the count of IPP exceeds the total count of pulse peaks in the same measurement unit time by a threshold (e.g., 15%, 20% or 25%). The atrial fibrillation (AF) may be determined when the irregular heart beat (IHB) is determined to exceed a threshold (e.g., 60%, 70% or 80%) in a plurality sets of measurement unit time. These conditions (such as IPP, IHB, AF, and HRV) may be categorized as one of the sub-collection of characteristics for determining the user's identity. It should be noted that, the Young's modulus $E=E_o e^{\alpha P}$ may be rewritten by changing dimension of $E=E_o e^{\alpha P}$ into mmHg to obtain $$\frac{E}{E_0} = \exp^{(\alpha P)},$$

and therefore the MK function $$PWV = \sqrt{\frac{hE}{dp}},$$

may be rewritten as $$MAP = \ln\left(\frac{PWV^2 \times D \times \rho}{h \times E_o}\right) \times \alpha$$

to obtain the intra-arterial pressure (P); wherein the intra-arterial pressure (P) may be considered as MAP.

According to the MK function, the relation between the blood vessel wall thickness (h), the blood vessel diameter (d) and the blood density (ρ) may be represented by $$PWV = \sqrt{\frac{hE}{dp}}.$$

The blood vessel diameter (d) and the blood density (ρ) may be determined by the processing unit 120 by utilizing diffuse reflectance spectroscopy (DRS) and diffuse optical imaging and tomography (DOT); the DRS and the DOT may be performed by using a MRS sensor of the sensors 110. When a medium of mixed fluid is measured by the MRS sensor, the total photons may equal a sum of absorption, reflection, and transmission. Absorption of the photons may be obtained based on Beer-Lambert law as $$\log\left(\frac{I_0(\lambda)}{I_t(\lambda)}\right) = \varepsilon L c.$$

Light transmission energy ($I_t$) is obtained by subtracting light attenuation energy (δI) from the light incidence energy ($I_0$) as described by $I_t = I_0 - \delta I$, and the δI is the sum of absorption and scattering. Accordingly, an attenuation coefficient (μ) may be broken down into absorption coefficient ($\mu_a$) and scattering coefficient ($\mu_s$). In addition, μ is a multiplication of molar concentration (c) and molar extinction coefficient (ε). When the medium of mixed fluid is blood, $\mu_a$ of the blood may be represented by hemoglobin (Hb) and oxyhemoglobin (HbO$_2$) as described by $\mu_a(\lambda) = 2.303\varepsilon_{Hb}(\lambda)c_{Hb} + 2.303\varepsilon_{HbO2}(\lambda)C_{HbO2}$. Preferably, $\mu_a$ of blood may be measured by the MRS sensor under the wavelengths of 420 nm and 940 nm; however, the wavelength is not limited thereto. Therefore, when distance of light path (L) is considered, the Beer-Lambert law may be rewritten as $I_t(L) = I_0 \times \exp^{-(\mu_a + \mu_s)L}$ and $I(L) = I_0 \times \exp^{-\mu_a L}$, which demonstrates that $I_t$ decreases with increasing L.

An absorption coefficient $\mu_a$ of the Hb may be represented by $\mu_a^{Hb} = k(\lambda) \cdot \gamma \cdot \mu_a^{blood}(\lambda)$, wherein γ is blood volume fraction and k(λ) is a calibration coefficient for $\mu_a^{Hb}(\lambda)$ at a specific wavelength λ, and $\mu_a^{blood}(\lambda)$ is the absorption coefficient of blood at the specific wavelength λ. The $\mu_a^{blood}$ may be expressed by ratio of hemoglobin absorption coefficient ($\mu_a^{Hb}$) and oxyhemoglobin absorption coefficient ($\mu_a^{HbO_2}$) in the whole blood. The γ may be expressed as $$Y = \frac{cHb}{150} = \frac{\text{plasma volume}}{1 - \text{Red Blood cells} * RBC_s)}$$

and measured by the MRS sensor. Therefore, absorption coefficient $\mu_a$ of the blood may be determined by $\mu_a^{blood}(\lambda) = 0.1 \ln 10 \times 150[\alpha 2.303\varepsilon_{HbO_2}(\lambda) + (1-\alpha)2.303\varepsilon_{Hb}(\lambda)]$, wherein α is oxygen saturation SPO$_2$ in percentage as measured by the NIRS. Accordingly, the absorption coefficient $\mu_a$ of the Hb and the absorption coefficient $\mu_a$ of the blood may be determined by the oxygen saturation SPO$_2$, and hence k(k) may be determined by the processing unit 120 according to $\mu_a^{Hb}=k(\lambda)\cdot\gamma\cdot\mu_a^{blood}(\lambda)$. In addition, the calibration coefficient $k(\lambda)$ may be expressed by $$k(\lambda) = \frac{1 - e^{-2\mu_a^{blood}(\lambda)r}}{2r\mu_a^{blood}(\lambda)};$$

therefore, the blood vessel diameter (d) may be determined by the blood vessel radius (r).

In at least one embodiment of the present disclosure, a method for determining blood vessel diameter (d) or blood vessel radius (r) is provided. According to Beer-Lambert law, absorbance is positively correlated to the concentration of absorbing species, when a homogeneous medium is irradiated by a diffuse reflection light source. However, when a blood vessel covered by the human tissues, such as the epidermis layer, the dermis layer, connective tissues, and fat, is irradiated by the light source at a specific wavelength that follows Beer-Lambert law, the absorbance of the blood vessel fluctuates with quantitative variation of red blood cells due to Windkessel effect. The fluctuation is a pulsatile alternating current (AC) component generated by the human body under a diffuse reflection light source, and is measurable as signals of reflectance and transmission by a photoelectric sensor among the sensors 110.

Figure 30:
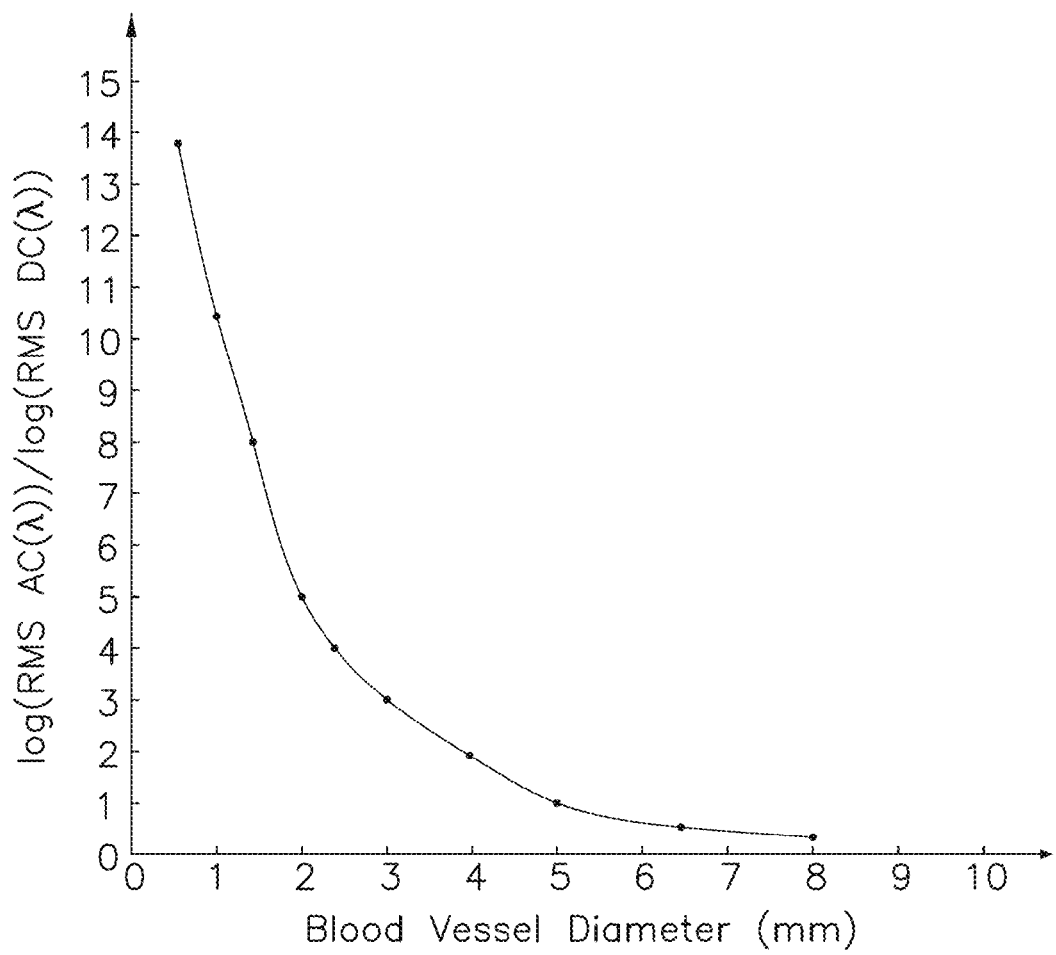
FIG. 30 a schematic illustration of a relationship between an AC/DC component ratio and blood vessel diameter in accordance with one embodiment of the present disclosure.

Outside of the range of the fluctuation, the rest of the absorbance measured by the photoelectric sensor is a non-pulsatile direct current (DC) component. Under the same external condition, a ratio of the AC component and the DC component $$\frac{\text{RMS AC}(\lambda_1)}{\text{RMS DC}(\lambda_2)}$$

should be identical for the same vessel size and red blood cell. As shown in FIG. 30, the ratio may vary linearly or non-linearly with the red blood cell. Capacity of the blood vessel depends on the blood vessel radius (r), and therefore quantitative quantification of blood vessel diameter (d) or blood vessel radius (r) may be realized. However, a photoplethysmography sensor used for measuring defuse reflection must have auto gain control for dynamic adjustment of irradiance or optical fluence rate; in addition, sensor placement positions and body tissue compositions would both affect models of absorption, reflectance, transmission, and scattering (which may be collectively referred to as an ARTS model). Therefore, irradiance or optical fluence rates should be normalized, and difference in the ARTS models should be corrected.

Figure 31:
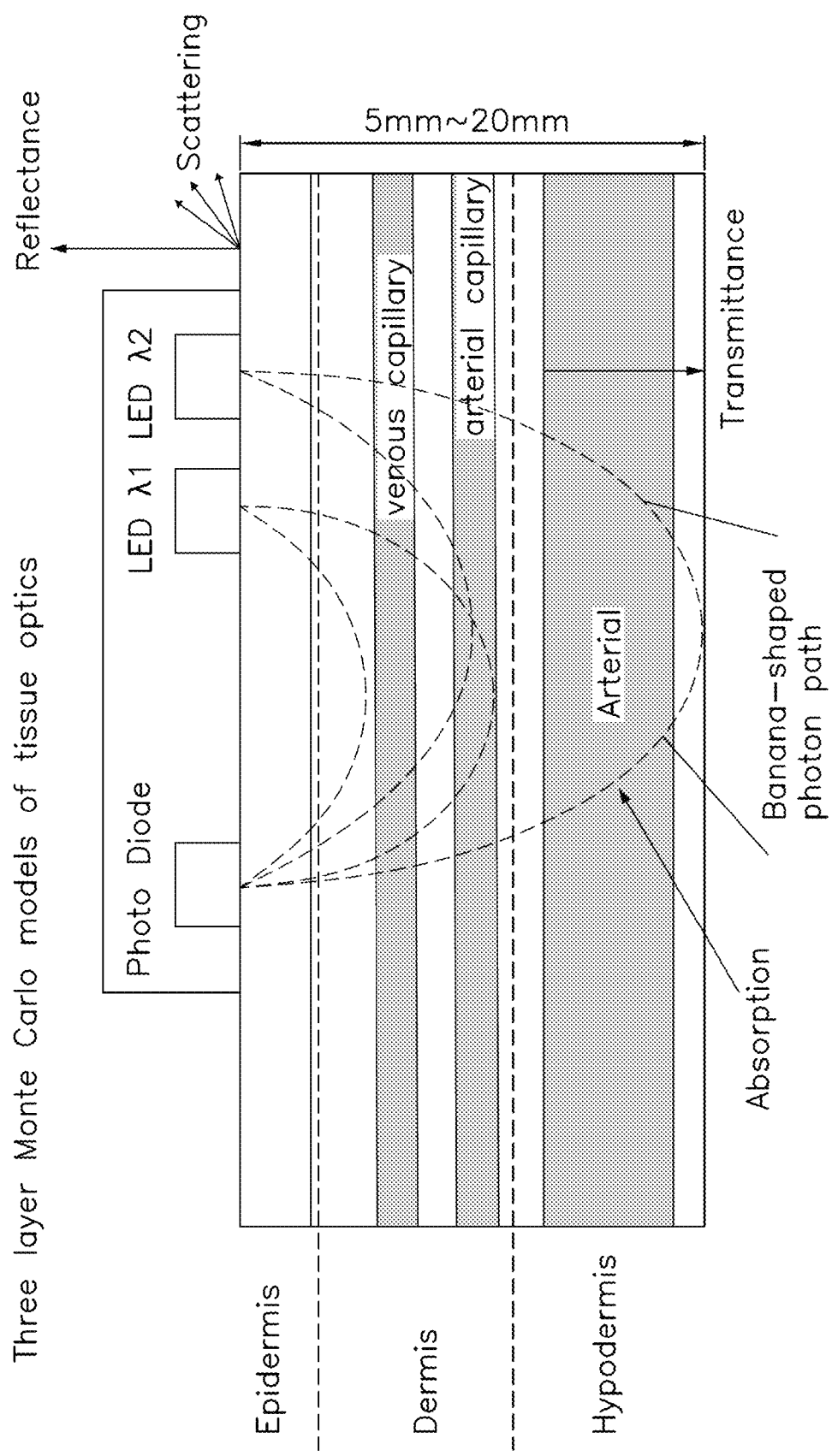
FIG. 31 a schematic cross-sectional illustration of a skin surface three layer Monte Carlo model of tissue optic at a forearm of a user in accordance with one embodiment of the present disclosure.

As shown in FIG. 31, numerical modelling of skin surface tissues and photoelectric sensors may be carried out in advance for the physiological signal monitoring system, and Monte Carlo method may be used to simulate the transmission process of large quantity of photons for the ARTS model. In the Monte Carlo simulated computed numerical model, light source quantity, light source position, light source wavelength, light receiving sensor quantity, light receiving sensor position are known and preset in the model, and the positions of the light receiving sensor may include absolute positions and relative positions. Multilayered tissue model may be utilized for simulations of skin surface tissue and blood vessel. The multilayered tissue model mainly includes three layers, which are epidermis, dermis, and blood vessel. Other well-known experimental parameters such as absorption coefficient, scattering coefficient, refractive index, and Henyey-Greenstein function may be used in the multilayered tissue model as well. The refractive index for a medium, such as glass, acrylic, or air, between the photoelectric sensor and a skin surface tissue may also be included in the input model.

Figure 32:
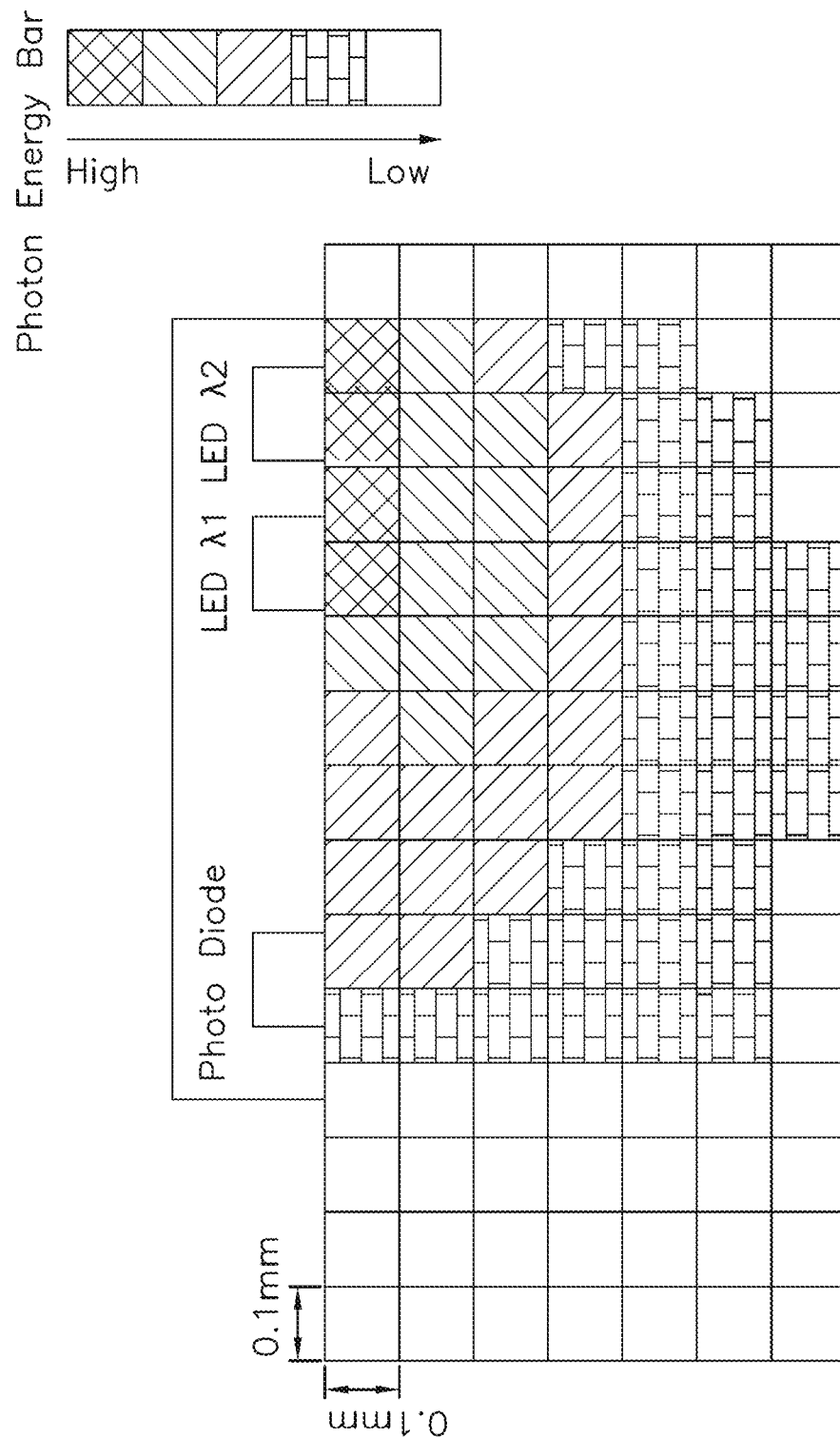
FIG. 32 a schematic illustration of a segmented skin surface model in accordance with one embodiment of the present disclosure.

As shown in FIG. 32, the skin surface tissue model may be segmented into a plurality of 0.1 mm squares for obtaining parameters of overall distribution. The transmission process of large quantity of photons may be simulated by a predictive ARTS model. The predictive ARTS model is then used for fitting and calibration of photoelectric sensors in the wearable device 100, as well as for inverse Monte Carlo fitting and calibration. Each calibration of optic measurements by the photoelectric sensors, the obtained AC component and the DC component may be normalized by the processing unit 120 according to equation $$\frac{\log[\text{RMS AC}(\lambda_1)]}{\log[\text{RMS DC}(\lambda_2)]},$$

and a ratio between the AC component and the DC component may represent a ratio between a single blood vessel diameter and the amount of whole blood in the blood vessel. Therefore, realizing quantification of blood vessel diameter (d) or radius (r) by the processing unit 120 may be realized. It should be noted that the core of this embodiment is to determine blood vessel diameter (d) or blood vessel radius (r) by quantifying the AC component and the DC component through calibrating deviations of actual measurements in the wearable device 100, and therefore is not limited to the above exemplary numerical values or parameters.

The relationship between the red blood cell (i.e., Hb and $HbO_2$) and blood plasma may be measured by the NIRS sensor. Normal whole blood is composed of about 55% of blood plasma and 45% of blood cell. More specifically, the blood plasma is composed of 92% of water and the remaining 8% is the combination of plasma proteins, and the blood cell is composed of 90% of red blood cell (i.e., Hb and $HbO_2$) and the remaining 10% are white blood cell and platelet. The densities of blood plasma and blood cell are known to be about 1.025 g/ml and 1.115 g/ml respectively; therefore, the blood density ($\rho$) of whole blood may be determined based on the densities and approximated between 1.03 g/ml to 1.075 g/ml for a normal healthy person. A calibration coefficient for calibrating the blood density ($\rho$) may be obtained from statistical data measured by a NIRS sensor, and is adjustable based on different conditions of different users; therefore, the blood density ($\rho$) is not limited to the aforementioned. Given the conditions that the parameters of the blood vessel diameter (d) and the blood density ($\rho$) are known, the thickness of the blood vessel wall thickness (h) may be determined by the processing unit 120 by utilizing statistical linear or non-linear regression with the MK function; in which the blood vessel wall thick (h) is assumed to be constant for every individual based on the known parameters of the blood vessel diameter (d), the blood density ($\rho$) and the calibrated PWV.

Figure 33:
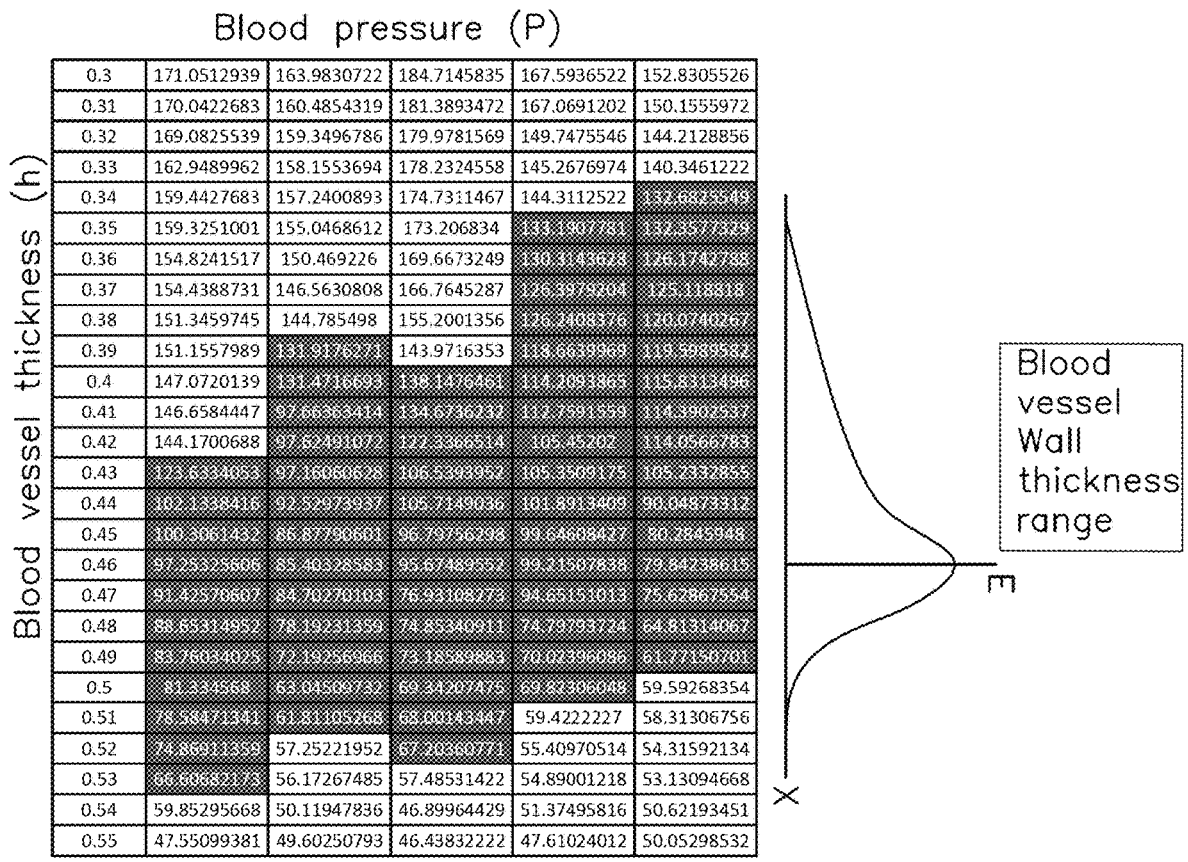
FIG. 33 a schematic illustration of a statistical analysis of an actual range of blood vessel wall thickness in accordance with one embodiment of the present disclosure.

In at least one embodiment of the present disclosure, another method for determining blood vessel wall thickness (h) is provided. It is known that blood pressure does not fluctuate significantly within a measurement unit time of approximately 15 seconds to 1 min, and that blood vessel diameter (d) and blood density ($\rho$) are known parameters. However, artery at different parts of body has different blood vessel effective radius r and blood vessel wall thickness (h). By incrementally increasing blood vessel wall thickness (h) by 0.01 mm from 0.01 mm to 1 mm, and taking the values of blood vessel wall thickness (h), blood vessel diameter (d), blood density (ρ), and pulse transit time (PTT) or pulse wave velocity (PWM) into the MK function to obtain blood pressure (P), a curve of "blood vessel wall thickness (h) versus blood pressure (P)" with 100 calculation points may be plotted. The blood pressure (P) determination may be repeated by the processing unit 120 using multiple values of PTT or PWM obtained within a measurement unit time, to obtain multiple sets of "blood vessel wall thickness (h) versus blood pressure (P)" curves. For every value of blood vessel wall thickness (h) on the multiple sets of "blood vessel wall thickness (h) versus blood pressure (P)" curves, points with reasonable values of blood pressure (P), such as between 60 mmHg to 140 mmHg, are selected for statistical analysis. Therefore, as exemplified in FIG. 33, the most common values of blood vessel wall thickness (h) correspond to an actual range of blood vessel wall thickness (h). It should be noted that, range of blood vessel wall thickness (h) may vary by various parts of the human body, and therefore the present disclosure is not limited to the aforementioned.

In order to determine value of $E_0$ and $\alpha$ in the wearable device 100, a series of pre-calibration and experimental statistics may be performed; $E_0$ and $\alpha$ are part of Young's modulus related to human arterial tissues. According to previous research studies, $E_0$ is approximately 1428.7 mmHg, and $\alpha$ falls between 0.015 and 0.033 mmHg. However, deviations may exist in the physiological signal monitoring system when determining the pulse transit time (PTT). Therefore, in at least one embodiment of the present disclosure, a method for calibration and determination of $E_0$ and $\alpha$ in the physiological signal monitoring system is provided. The wearable device 100 may be attached to a simulator (not shown), wherein a set of PTT ($\alpha 0n$) simulated by the simulator are compared to a set of PTT($\alpha 1n$) measured by the wearable device 100, to obtain a transformation function between the PTT ($\alpha 0n$) and the PTT($\alpha 1n$) as represented by $$\begin{bmatrix} a_0, 1 \\ a_0, 2 \\ \vdots \\ a_0, n \end{bmatrix} = a \cdot \begin{bmatrix} a_1, 1 \\ a_1, 2 \\ \vdots \\ a_1, n \end{bmatrix} + b.$$

Therefore, the transformation function, which is a representation of deviation in PTT measurements of the wearable device 100 due to variation in $E_0$ and $\alpha$, may be preset in the processing unit 120. It should be noted that any arithmetic values mentioned in this embodiment is only for explanation, and thus do not limited the embodiments of the present disclosure.

Figure 34:
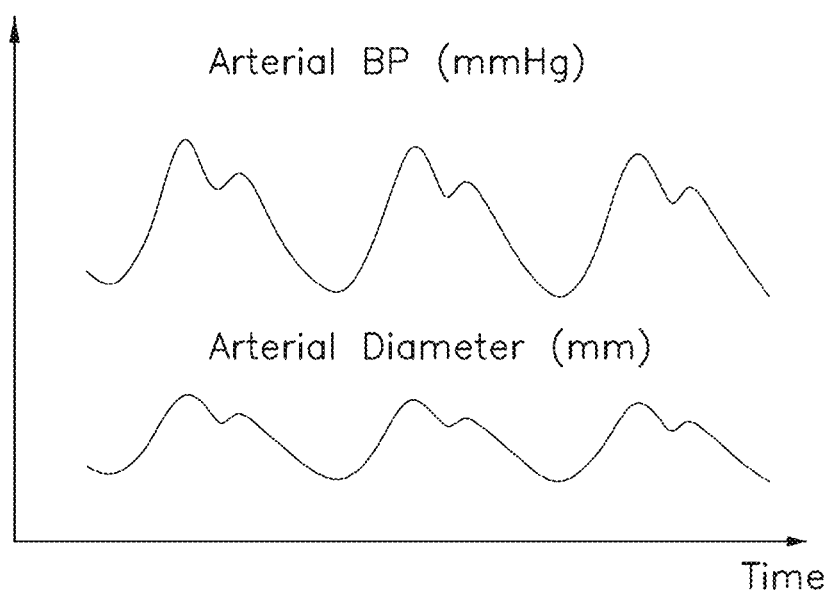
FIG. 34 a schematic illustration of a relationship between an arterial blood pressure and arterial diameter in accordance with one embodiment of the present disclosure.
Figure 35:
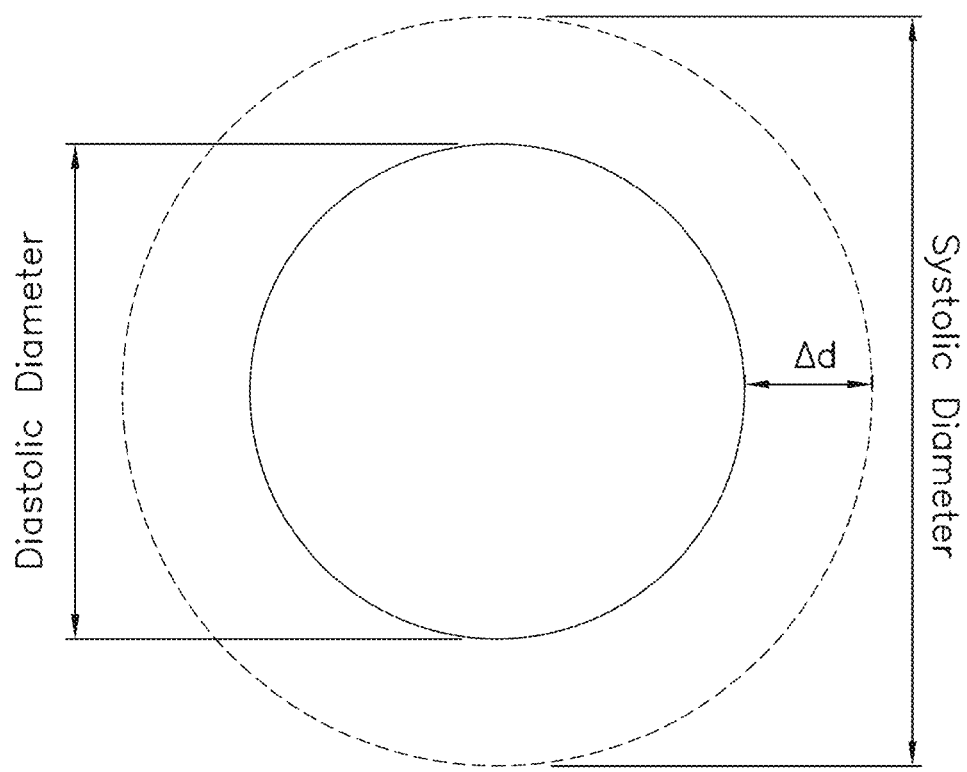
FIG. 35 a schematic illustration of diastolic and systolic blood vessel diameters in accordance with one embodiment of the present disclosure.

Normally, pulse pressure (PP) ranges from 30 mmHg to 50 mmHg. However, in cases of cardiovascular disease or arterial disease, the PP can range from 30 mmHg to 100 mmHg. In at least one embodiment of the present disclosure, a method for determining PP by photoplethysmogram intensity ratio (PIR) and pulse transit time (PTT) is provided. As shown in FIG. 34 and FIG. 35, PP is related to expansion of artery diameter, that can be represented by the PIR; therefore, one's PIR may be linear or non-linear under different PPs. Therefore, the variation of PP must be normalized according to the arterial stiffness level. Since the arterial stiffness level, as represented by $E_0$ and $\alpha$ in $$PWV = \sqrt{\frac{hE_0 \exp^{(\alpha \cdot P)}}{d\rho}},$$

is positively correlated with PTT, a set of arterial stiffness values may be determined by the processing unit 120 using a set of PTT values obtained from the sensors 110; and the PIR may be determined by the processing unit 120 according to $$I_L = I_0 \times e^{-\alpha \cdot DC \cdot d \cdot DC} \times e^{-\alpha \cdot D_s}$$

$$I_H = I_0 \times e^{-\alpha \cdot DC \cdot d \cdot DC} \times e^{-\alpha \cdot D_d}$$

$$\Delta d = D_s - D_d = \frac{1}{a} \cdot \ln \frac{I_H}{I_L}$$

Hence, the PIR measurements are normalized by the set of arterial stiffness levels by the processing unit 120, and the normalized PIR may be utilized for determining PP via a look-up table of arterial stiffness normalized PTR versus PP preset in the processing unit 120. It should be noted that the core of this embodiment is to determine PP by arterial expansion level, and therefore does not limit the embodiments of the present disclosure.

Figure 36:
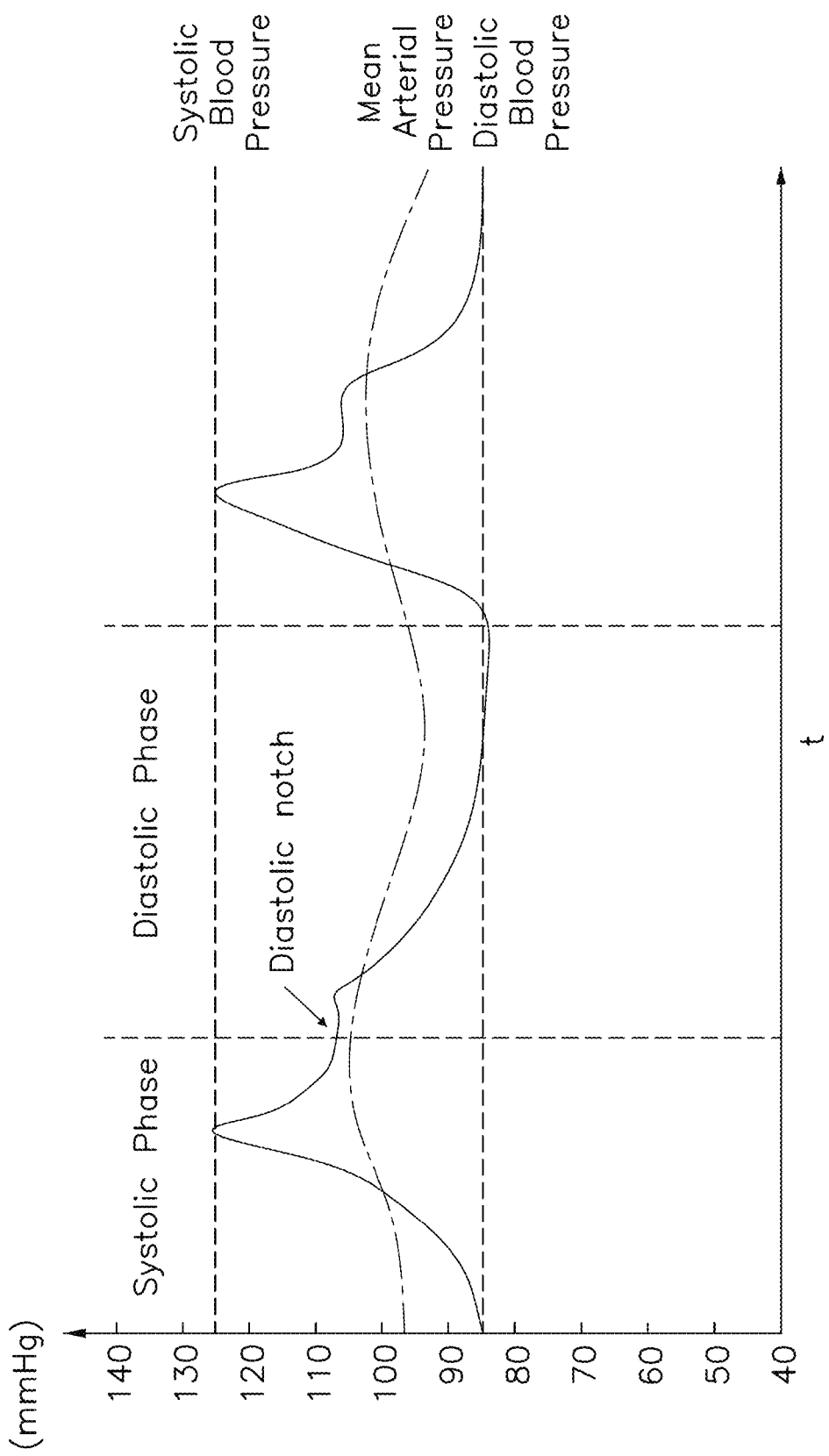
FIG. 36 a schematic illustration of a relationship between systolic blood pressure, mean arterial pressure, and diastolic blood pressure in accordance with one embodiment of the present disclosure.
Figure 37:
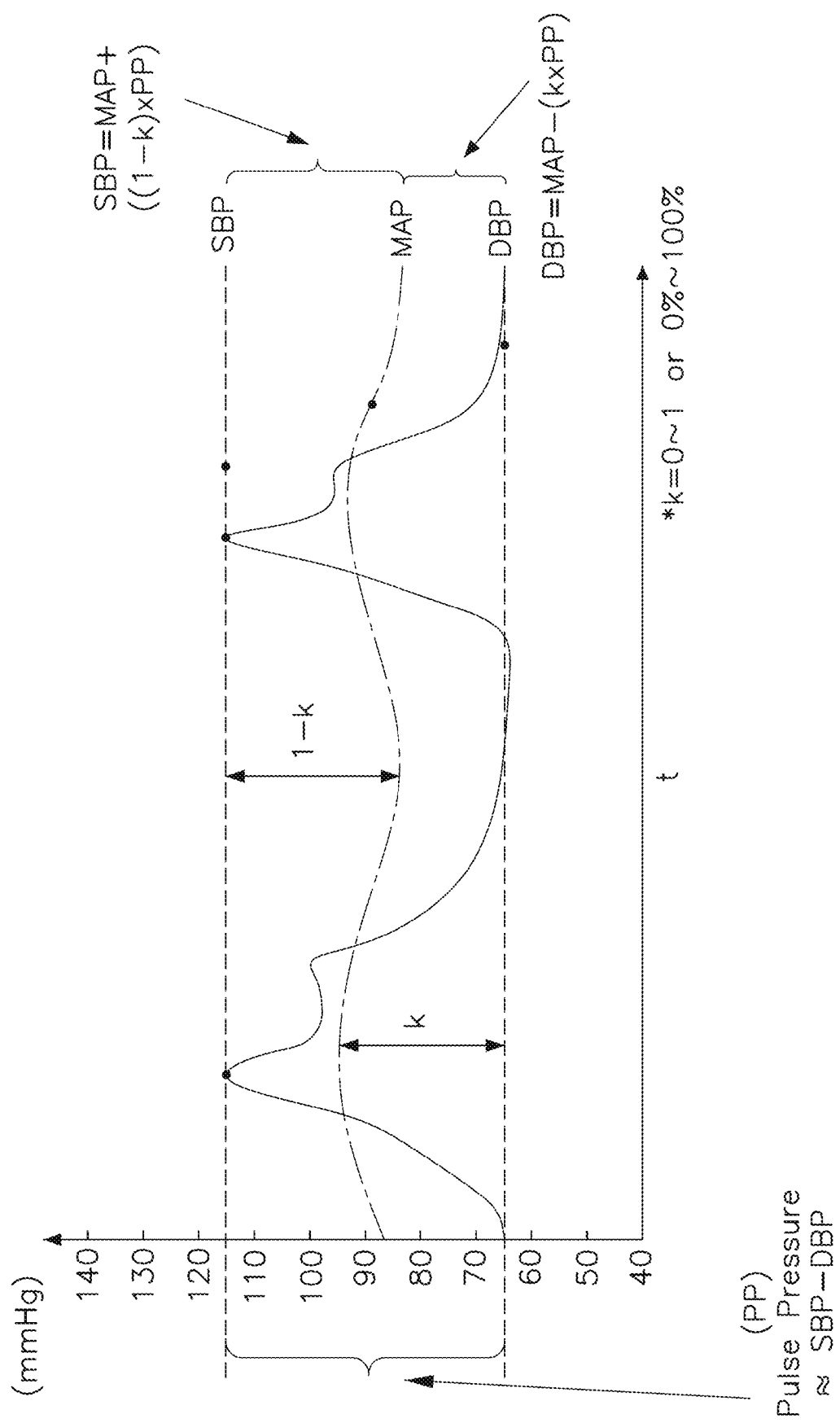
FIG. 37 a schematic illustration of a relationship between systolic blood pressure, pulse pressure, and diastolic blood pressure in accordance with one embodiment of the present disclosure.

In at least one embodiment of the present disclosure, an algorithm for determining the systolic blood pressure (SBP) and the diastolic blood pressure (DBP) is provided. The difference between the SBP and the DBP may be referred to as pulse pressure (PP), which is the pressure generated by pulse of cardiac contraction, and may be determined as PP=SBP−DBP. As heart rate increases, the mean arterial pressure (MAP) becomes closer to the arithmetic mean of the SBP and the DBP; as shown in FIG. 36, the MAP lies between SBP and DBP. Therefore, relationships between MAP, SBP, DBP and PP may be used for determining the SBP and the DBP by introducing a coefficient k to the MAP and the PP, wherein the coefficient k ranges from 0 to 1. As shown in FIG. 37, when the coefficient k is adjusted in DBP=MAP−(k×PP) and SBP=MAP+(1−k)·P the SBP and DBP may be determined by the processing unit 120 by adjusting the MAP value up and down with PP. It should be noted that, though the coefficient k is the core for determining the SBP and the DBP, embodiments of the present disclosure should not be limited to only a single coefficient.

In at least one embodiment of the present disclosure, a method for sampling pulse transit time (PTT) or pulse wave velocity (PWV) may be performed by measuring a time difference of an arterial pulsation between different measuring points by the sensors 110; wherein the time difference may represent the PTT or PWV. A known fact in the field of instrument measurement is that instrumental measurements are presented in the form of Gaussian distribution, including actual values and errors, wherein the errors may include systematic errors and random errors. Therefore, when a set of PTT or PWV is measured in a unit time, the values sampled thereof must be determined by numerical methods. For example, a median or average number may be determined by the processing unit 120 from a group of PTT or PWV to determine an actual value representing of PTT or PWV. The method of obtaining the actual values represented by PTT or PWV in the present disclosure is not limited thereto.

In at least one embodiment of the present disclosure, the actual value determination of the heart rate, pulse transit time (PTT), and pulse wave velocity (PWV) may be realized by statistical methods. Therefore, successful measurement during determination of the actual values may be determined by the processing unit 120 according to degree of dispersion per measurement unit time. For example, through determination of variance of Gaussian distributions, any physiological signals received by the sensor 110 with large dispersion may be determined as not satisfying when variance of the physiological signals exceeds a threshold. In such case, a visual and/or audio notification may be generated by the alarm or display for prompting a retest.

Figure 38:
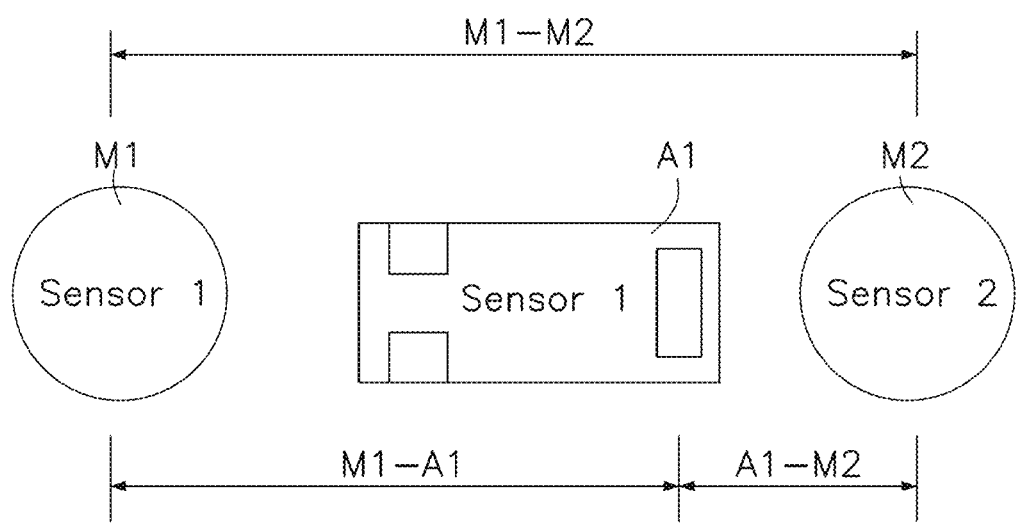
FIG. 38 a schematic illustration of a wearable device including two major sensors and one auxiliary sensor in accordance with one embodiment of the present disclosure.
Figure 39:
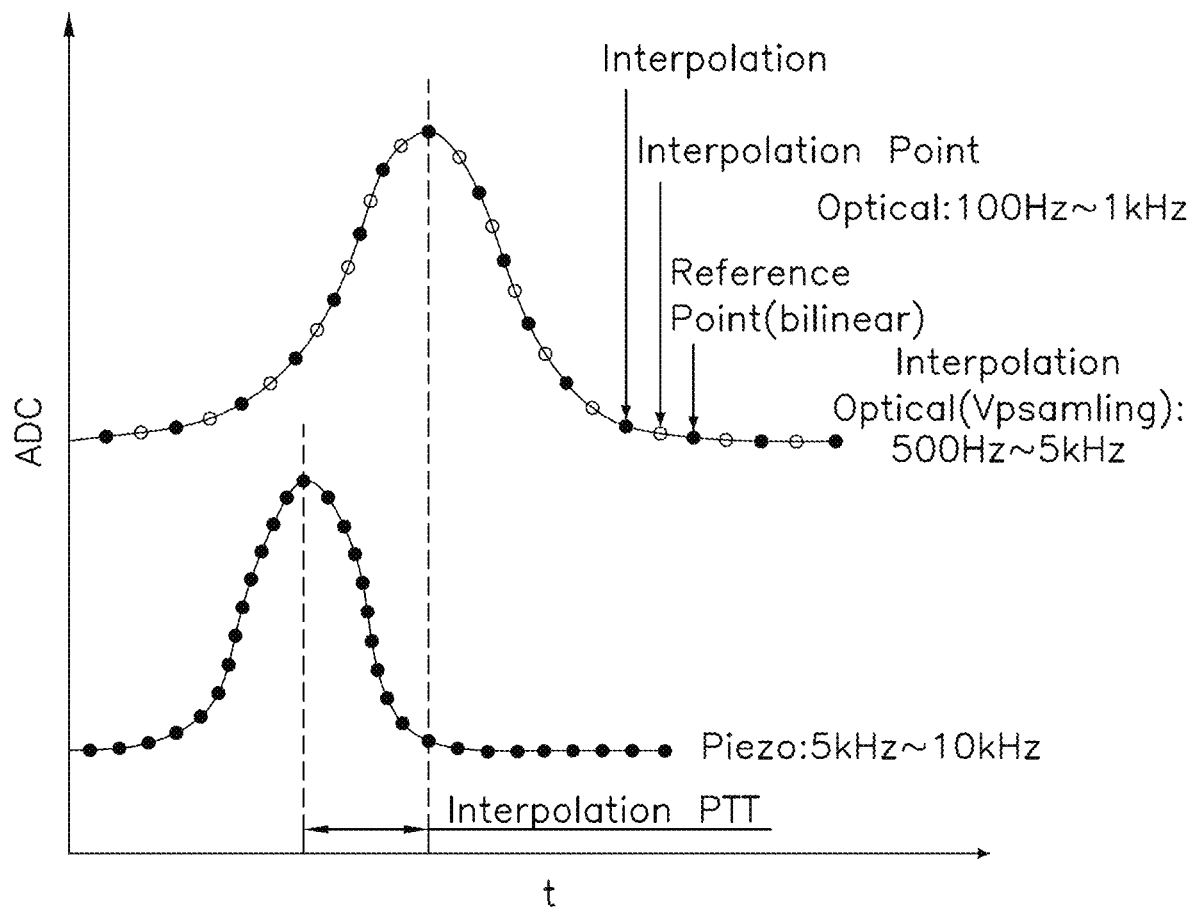
FIG. 39 a schematic illustration of an interpolation applied to one sensor with low sampling rate in accordance with one embodiment of the present disclosure.

In at least one embodiment of the present disclosure, a determination method of pulse transit time (PTT) by multiple sensors 110 is provided. The sensors 110 of the wearable device 100 include major sensors and auxiliary sensors. Values of PTT obtained by the major sensors and by the auxiliary sensors may be cross referenced to each other during PTT determination. However, sampling rates of the major sensors and auxiliary sensors are different; therefore, a specific algorithm may be designed for the determination. For example, for the wearable device 100 including two major sensors M1 and M2, and an auxiliary sensor A1 as shown in FIG. 38, three values of PTT, which are M1-M2, M1-A1, and M2-A1, may be obtained. It should be noted that one with higher sampling rate among the major sensors M1, M2 and the auxiliary sensor A1 dominates in the determination. Hence, as shown in FIG. 39, interpolation is applied between the sensing points (i.e., the peak or trough points) of the one with lower sampling rate. The interpolation may be linear interpolation, bilinear interpolation, or any other interpolation. Local maximum or local minimum may be determined by the processing unit 120 in N interpolation points from a peak point or a trough point, respectively, wherein N equals to a ratio of the high sampling rate over the low sampling rate. Therefore, as shown in FIG. 39, the local maximum or local minimum may be used with the corresponding pulse peak or pulse trough obtained from the sensor with higher sampling rate for PTT determination. It should be noted that the core of this embodiment is to determine PTT with the sensors 110 having different sampling rates by the wearable device 100, and therefore is not limited to the above exemplary numerical values or parameters.

In at least one embodiment of the present disclosure, a heart rate determination method is based on measurements of pulse waves of arterial pulsations by the sensors 110. Beat per minutes (BPM) may be determined according to the time difference between a current pulse at time t and a previous pulse at time t−1. Since N pulses may be obtained within a measurement unit time, a total number of periods between pulses is N−1. The heart rate may be determined by the processing unit 120 as a median or average number of N−1, and the determined heart rate may represent a heart rate within the measurement unit time. The method for obtaining heart rate in the present disclosure is not limited thereto.

Within the context of the present disclosure, the terms "feature extraction" and "classification method" refer to the process or technique of forming a collection of each of the characteristics of the physiological signals acquired from the sensors such as ECG, EMG, piezoelectric or the like, such sensors may also belong to sub-collections thereof. The collection of the characteristics of the physiological signals may be classified into different categories by the classification methods, such as principal component analysis (PCA), linear discriminant analysis (LDA), locally linear embedding (LLE) or Laplacian Eigenmaps. Through classification, characteristics that have large covariance values may be classified into additional categories to output a new collection of the characteristics that has a lower dimension than that of the original collection. The new collection may be trained by classifiers to determine the user's identity. The classifiers may be programmed based on conventional machine learning methods, such as support vector machine (SVM), linear regression, logistic regression, decision tree, k neighbors or Naive Bayes. After the user's identity is determined, the physiological signals and the physiological information of the user 101 may be stored on the mobile devices 200 or the cloud server 300 according to the user's identity. The classification method may only be performed on the mobile devices 200 or on the cloud servers 300, while the wearable device 100 may only acquire the physiological signals and the physiological information, and transmit to the mobile devices 200 and the cloud servers 300.

In at least one embodiment of the present disclosure, the sensors 110 may include a pair of electrodes for reading continuous signal of electromyography (EMG) from a wrist. When any signal reading is determined larger than a root mean square (RMS) value of the continuous signal by the processing unit 120, the signal may be a sub-collection of the characteristics of the physiological signals for determining the user's identity. The continuous signal may be processed by Fast Fourier Transform (FFT) to obtain a frequency spectrum, so as to form another sub-collection of characteristics for user identification.

In at least one embodiment of the present disclosure, the sensors 110 may include two pairs of electrodes; one pair of electrodes is connected to a general-purpose input/output (GPIO) of a pulse wave modulation (PWM) generator or a digital-analog convertor (DAC) waveform generator to apply a combination of different AC signals having different frequencies, such as 5 k, 10 k, 50 k, 100 k, 500 k and 1M Hz, on the surface of the skin. At the same time, the other pair of electrodes detects variations in the AC signals to allow derivation of the impedance of the skin and body fat through an RLC model and frequency spectrum analysis by the processing unit 120. In addition, each user has a distinct and complicated composition of skin, such as cuticle, connective tissue, fat and moisture content. Therefore, the acquired frequency spectrum may be another sub-collection of characteristics for determining the user's identity.

In at least one embodiment of the present disclosure, the sensors 110 may include a near-infrared spectroscopy (NIRS) sensor formed by laser diodes or LED(s) having a wavelength ranging from 300 nm to 1100 nm and photodiode(s) configured to detect the same wavelength. A Monte Carlo simulation may be performed for absorption, reflection, and transmission according to geometric optical characteristics of the NIRS sensor, such that an ART (i.e., absorption, reflection, transmission) model of the NIRS sensor is generated for calibration. The NIRS sensor may detect the ratios of various blood contents including oxidative hemoglobin ($HbO_2$), hemoglobin (Hb) and blood glucose to allow determination of the corresponding $SpO_2$, $SaO_2$, and blood flow for calibrating at least one coefficient of the Moens-Korteweg (MK) function by the processing unit 120. The characteristics of dicrotic notch in photoplethysmography (PPG) signals may be used to analyze the properties of heart and artery, such as the relationship of hypertension and cardiac cycle. Therefore, the acquired characteristics from PGG may further represent one of a sub-collection of characteristics for determining the user's identity.

In at least one embodiment of the present disclosure, the sensors 110 may be a pair of electrodes to retrieve modified limb lead II (MLII) electrocardiography (ECG) signals. Detecting the R wave crest of QRS complex may be utilized to determine irregular pulse peak (IPP), irregular heart beat (IHB), atrial fibrillation (AF), heart rate variability (HRV) and heart rate by the processing unit 120. The PQRST wave of the ECG signals may present the whole cardiac cycle, therefore, time domain signals of the PQRST may be one of a sub-collection of characteristics for determining the user's identity.

In at least one embodiment of the present disclosure, a photon transport simulation with the Monte Carlo method requires calibration in response to different types of skin tissue, therefore a curve fitting of the results from the photon transport simulation and actual measurements according to Fitzpatrick classification may be applied. The photon transport simulation may be performed with optical parameters under different wavelengths, strengths, positions of LEDs, and different sizes and positions of photo-electric sensors. The optical parameters of different skin types according to the Fitzpatrick classification may include refractive index, scattering rate, absorption rate, and Henyey-greenstein function. Results of the photon transport simulation associated with different skin types according to the Fitzpatrick classification may include absorption, reflection, transmission, and scattering. The actual measurements may be carried out by a "Mechanical Wave Time Delay Structure/Pulse Transit Time Rescale" method on different skin types according to the Fitzpatrick classification. Hence, the calibration may be carried out by the curve fitting of the results from the photon transport simulation and the actual measurements.

In at least one embodiment of the present disclosure, a multi-layer tissue model, a micro blood vessel random distribution model, and an artery random distribution model are built by Monte Carlo simulations under different wavelengths of light sources and different light sensors; and results of the simulation are representations of specific type of tissue model under specific wavelengths of light source. Hence, a "Light Source-Light Sensor-Tissue Model" lookup table may be built by combining the results of the simulation. When actual measurements are performed by the sensors 110, the "Light Source-Light Sensor-Tissue Model" lookup table may be used by the processing unit 120 to calibrate deviation of the actual measurements. In addition, an inverse Monte Carlo simulation may also be applied to the "Light Source-Light Sensor-Tissue Model" lookup table, in designing a light sensor accordingly. Overall, one of the core of the present disclosure is the application of Monte Carlo method followed by forward or backward curve fitting, which may be used as a reference for calibrating actual measurements or for designing optical sensors, respectively.

In sum, the device and method according to the various embodiments of the present disclosure utilize pulse transit time and hemodynamic parameters to ensure high accuracy of blood pressure monitoring, improved wearing experience, and convenient monitoring.

Previous descriptions are only embodiments of the present disclosure and are not intended to limit the scope of the present disclosure. Many variations and modifications according to the claims and specification of the disclosure are still within the scope of the claimed disclosure. In addition, each of the embodiments and claims does not have to achieve all the advantages or characteristics disclosed. Moreover, the abstract and the title only serve to facilitate searching patent documents and are not intended in any way to limit the scope of the claimed disclosure.

What is claimed is:

1. A device for measuring blood pressure, comprising:
a housing;
a processing unit disposed in the housing;
a display disposed on the housing and in communication with the processing unit;
a plurality of sensors in communication with the processing unit and configured to sense an artery of a user and transmit at least one physiological signal corresponding to the artery to the processing unit, the plurality of sensors comprises a piezoelectric sensor, an accelerometer and a gyroscope; and
a signal controller and a signal detector in communication with the piezoelectric sensor,
wherein the processing unit is configured to:
process the at least one physiological signal to obtain a plurality of hemodynamic parameters and a pulse transit time (PTT), the plurality of hemodynamic parameters comprising a blood vessel wall thickness, a blood vessel diameter, and a blood density,
determine a pulse wave velocity (PWV) as being equal to a distance between two of the plurality of sensors divided by the PTT,
determine a posture according to an axial change detected by the accelerometer and the gyroscope,
calibrate the PWV according to the posture by referencing a posture-to-PWV look up table stored in the processing unit, the posture-to-PWV look up table created by obtaining correction coefficients corresponding to different angles and angular acceleration received from the accelerometer and the gyroscope,
determine an intra-arterial pressure from the plurality of hemodynamic parameters and the calibrated PWV via a Moens-Korteweg (MK) function, and considering the intra-arterial pressure as a mean arterial pressure,
determine a set of arterial stiffness values using a set of PTT values,
obtain a photoplethysmogram intensity ratio (PIR) and normalizing the PIR by the set of arterial stiffness values,
determine a pulse pressure according to the normalized PIR via a look-up table of arterial stiffness normalized PIR versus pulse pressure (PP) stored in the processing unit, the PP being a difference between a systolic arterial pressure and a diastolic arterial pressure,
determine the systolic arterial pressure and the diastolic arterial pressure from the mean arterial pressure, and the PP and a coefficient k ranging from 0 to 1, and
control the display to display the systolic arterial pressure and the diastolic arterial pressure,
wherein the signal detector is configured to detect a first signal direction of at least one first physiological signal sent from the piezoelectric sensor, and when a polarization direction of the piezoelectric sensor is opposite to an expected polarization direction, the signal controller is configured to change a second signal direction of at least one second physiological signal subsequent to the at least one first physiological signal.

2. The device according to claim 1, wherein the plurality of sensors comprises a mechanical wave sensor and an optical sensor.

3. The device according to claim 2, wherein the mechanical wave sensor comprises the piezoelectric sensor, a plurality of through-holes on the housing is disposed corresponding to the piezoelectric sensor and the optical sensor, and the plurality of through-holes forms a straight line parallel to the artery.

4. The device according to claim 3, wherein the piezoelectric sensor and the optical sensor are configured to operate under different sampling rates.

5. The device according to claim 1, wherein the plurality of sensors comprises two mechanical wave sensors and an optical sensor, a plurality of through-holes on the housing is disposed corresponding to the two mechanical wave sensors and the optical sensor, and the plurality of through-holes forms a straight line parallel to the artery.

6. The device according to claim 5, wherein a sampling rate of the two mechanical wave sensors is different from a sampling rate of the optical sensor.

7. The device according to claim 1, further comprising: a time delay structure disposed between one of the plurality of sensors and one of a plurality of through-holes formed on the housing, wherein the time delay structure is configured to lengthen a path distance between a measurement point on the user and the one of the plurality of sensors, and the PTT obtained by the processing unit is associated with the path distance.

8. The device according to claim 7, wherein the time delay structure is spiral shaped or zig-zag shaped.

9. The device according to claim 7, wherein the time delay structure is a tube containing a medium for transmitting mechanical waves.

10. The device according to claim 1, wherein the device enters a measuring mode and displays the systolic arterial pressure and the diastolic arterial pressure when the posture of the user determined by the processing unit according to the axial change lasts for a period of time longer than a threshold.

11. The device according to claim 1, further comprising an alarm configured to generate a retest notification when variance of the at least one physiological signal is determined to exceed a threshold.

12. The device according to claim 1, wherein the plurality of sensors comprises a mechanical wave sensor, at least one of a plurality of through-holes formed on the housing is conical shaped and enhances reception of the mechanical wave sensor.

13. The device according to claim 1, further comprising a contacting material fixedly attached around an opening of a plurality of through-holes to enhance seal tightness between the opening and a skin surface of the user.

14. The device according to claim 1, further comprising a mesh material or a film covering one of a plurality of through-holes to prevent foreign objects from entering the plurality of through-holes.

15. The device according to claim 14, wherein the mesh material is made of polytetrafluoroethylene, and the film is made of silicone rubber.

16. The device according to claim 1, wherein the plurality of sensors is disposed in the housing and do not overlap a central line of the device.

17. The device according to claim 1, wherein each of the plurality of sensors is removably attached to the user and wired or wirelessly connected to the device.

18. The device according to claim 1, wherein the plurality of sensors comprises a first sensor and a second sensor, the first sensor is disposed outside of the housing of the device, and the second sensor is disposed in the housing.

* * * * *